United States Patent [19]

Gadgil et al.

[11] Patent Number: 5,780,860
[45] Date of Patent: Jul. 14, 1998

[54] UV WATER DISINFECTOR

[75] Inventors: Ashok Gadgil, El Cerrito, Calif.; Vikas Garud, Bombay, India

[73] Assignee: The Regents of the University of California, Oakland, Calif.

[21] Appl. No.: 692,558

[22] Filed: Aug. 6, 1996

Related U.S. Application Data

[60] Provisional application No. 60/003,485 Sep. 8, 1995.
[51] Int. Cl.[6] ............................................. A61L 2/10
[52] U.S. Cl. ................ 250/432 R; 250/434; 250/435; 422/24
[58] Field of Search ...................... 250/432 R, 434, 250/435; 422/24

[56] References Cited

U.S. PATENT DOCUMENTS

| | | | |
|---|---|---|---|
| 2,504,349 | 4/1950 | Prieto | 250/434 |
| 3,836,781 | 9/1974 | Ellison | 250/432 R |
| 4,102,645 | 7/1978 | Meacham, Jr. et al. | 250/432 R |
| 5,503,800 | 4/1996 | Free | 250/432 R |
| 5,635,133 | 6/1997 | Glazman | 250/432 R |

*Primary Examiner*—Kiet T. Nguyen
*Attorney, Agent, or Firm*—Knobbe, Martens, Olson & Bear, LLP

[57] ABSTRACT

A UV disinfector with a gravity driven feed water delivery system, and an air-suspended bare UV lamp. The disinfector is hydrodynamically optimized with a laminerizing, perforated baffle wall, beveled treatment chamber, and outlet weir.

41 Claims, 6 Drawing Sheets

UV WATER DISINFECTOR

This invention was made with U.S. Government support under Contract No. DE-AC03-76SF00098 between the U.S. Department of Energy and the University of California for the operation of Lawrence Berkeley National Laboratory. The U.S. Government has certain rights in this invention.

This application takes priority from provisional application number 60/003,485 filed Sep. 8, 1995.

BACKGROUND OF THE INVENTION

The invention is related to the UV disinfection of water and other liquid streams. Common challenges to UV water disinfection devices are assuring complete treatment of the water stream, and dealing with quartz or Teflon jacketed lamps. These jackets have the complications of high cost, as well as of leakage, fouling with biomasses, films and with chemical deposits.

Early UV Disinfection Devices

The first devices for the disinfection of drinking water with ultraviolet light were developed in the early nineteen hundreds. As with contemporary UV water disinfecters, these devices typically directed the untreated water flow around a UV lamp sealed in a quartz sleeve. This was done to utilize the rays being emitted from any direction and to assure complete treatment of the water.

Keys teaches a gravity driven water or milk sterilizer with a quartz sleeve for the UV lamp, and a cooling coil. Horizontal grooved baffles and channels are provide to direct the flow of the liquid to be treated [U.S. Pat. No. 1,307,500, issued Jun. 24th, 1919].

Pole teaches the use of a large container for the feed water, and then runs the water through a narrow channel past a quartz sleeved UV lamp twice, with mixing to more evenly distribute the water between treatments. These features were provided in an effort to fully treat the final product. A reflector was used to redirect divergent rays to the water [U.S. Pat. No. 1,367,090, issued Feb. 1st, 1921].

Some of the many early systems taught by Henri et al. had a lamp surrounded by quartz windows through which the feed water is irradiated. Heneri et al. teaches the use of a UV light in a quartz jacket to irradiate water during numerous radial passages near the light. Eddy currents are introduced by guides or baffle plates in the feed water [U.S. Pat. No. 1,200,940 issued Oct. 10th, 1916 and divisional U.S. Pat. No. 1,473,095, issued Nov. 6th, 1923]. In one Henri et al. patent, the feed water flows beneath the lamp within its quartz container [U.S. Pat. No. 1,193,143, issued Aug. 1st, 1916].

While these early systems provided the first models for later UV systems, they were rapidly displaced by more attractive and practical water disinfection approaches. The early UV device designs had very high operational costs. Also, the equipment proved to be unreliable and require a high level of maintenance. Chlorination soon became established as more efficient and reliable for water disinfection.

Modern UV Disinfection Devices

General UV technology has matured considerably since the turn of the century research efforts to provide practical UV water disinfection. UV technology has become less expensive, and the complex contemporary UV disinfection devices have recently been gaining popularity, particularly in Europe. While the treatment is still of very high cost, health concerns about standard chlorine disinfection have lead certain affluent communities to employ expensive modern UV disinfection devices to decrease their exposure to this chemical. By 1990, approximately 2000 municipal water treatment plants in Europe were using UV disinfection systems.

Contemporary systems typically require complex circulation schemes. Because the submerged UV lamps require a quartz jacket regularly subject to mineral and biomass build up, many systems are provided with mechanisms which continually clean these surfaces [Hippen, U.S. Pat. No. 3,562,520, issued Feb. 9th, 1971; Ellner, U.S. Pat. No. 4,899,056 issued Feb. 6, 1990]. Partial submersion of lamps during variable flow has been taught [Tipon, U.S. Pat. No. 5,208,461, issued May 4, 1993]. Jacketing the feed water in a coil about the lamp has also been used [Noll, et al., India Patent Application No. 373/CAL/87, May 7th, 1991].

Because of the disinfection limitations of current UV systems, UV devices have been developed which combine other disinfection methods to assure full safety of the treated water. Flatow teaches the combination of multiple UV lamps and supplementing UV treatment with ozone for additional disinfection [U.S. Pat. No. 4,204,965, issued May 27, 1980]. Mortensen teaches purifying the feed water with an activated carbon filter prior to UV treatment [U.S. Pat. No. 4,615,799, issued Oct. 7th, 1986], as does Lin [U.S. Pat. No. 4,902,411, issued Feb. 20, 1990].

Water Treatment Techniques in Developing Nations

Disinfection of community water supplies is uncommon in developing countries. Particular problems are faced by these communities in obtaining safe drinking water because of severe limitations of public investment in safe water supply, shortage of skilled personnel, irregular supply delivery, and isolation. For instance, during the monsoon season, water born pathogens often flood the usual water supply. At the same time the community is cut off from medical help and safe water sources. As a result, many lives are lost.

Deep tubewells are a typical source of drinking water for many rural families in such countries as India. Because the wells are more that 200 feet deep, the water has been sealed beneath an impermeable layer of earth for a long time and is commonly bacteria-free. Unfortunately, deep tubewells can be expensive and time consuming to construct because of the specialized deep-drilling equipment that is required. These limitations make this source of water unavailable to many rural communities.

Disinfection with chlorine bleach is another method used by rural communities to provide safe drinking water. This method kills all pathogen, including giardia. Additionally, if bacteria a reintroduced into a chlorinated water supply, the new bacteria will die. A limitation to this technique in rural areas is that it is easy to overdose water with chlorine, thus requiring often unavailable trained personnel to test chlorine levels before the treated water is consumed. Of critical importance is that a steady supply of chlorine bleach is required to provide disinfection. This limitation was considered a major cause for the 1994 cholera outbreak in India when there was a breakdown in the supply chain for chlorine bleach to a number of rural areas.

Boiling drinking water over a cook stove to make it safe is a common practice in some developing countries such as China. This age old approach is effective in eliminating water born pathogens. However, with the deforestation of large areas, collection of fuel wood has become difficult and sanitary water more imperiled. Additionally, there are serious health risks associated with smoke inhalation from biomass-fueled traditional cook stoves.

The advent of a UV water disinfector that could bring the advantages of safe drinking water to developing nations at a low cost would represent an important advancement in the field. Such a device would improve and potentially save the lives of millions of people.

SUMMARY OF THE INVENTION

The inventive UV disinfector represents a critical advancement in providing safe water to the people of developing countries. A very low energy UV lamp is all that is required to treat large amounts of water because of the innovative, optimized flow design including a laminarize baffel wall and beveled treatment tray. The progression of the water through the system is powered solely by gravity. Built in safety features assures water quality and the safety of even unskilled users. The unique qualities of the inventive UV water disinfector will allow whole villages in rural and underdeveloped regions of the world to enjoy the advantages of safe water which is not available to them presently. The decrease in infant deaths and general illness that will result from the use of disinfection units based on the inventive principles will be of critical importance to these communities.

The carefully designed flow rate and pattern of the inventive device is accomplished with baffles outside of the treatment chamber, angled chamber walls, and specially configured treatment trays and inlet and outflow ports. Gravitational force is relied upon to power the flow of water eliminating the need for the pumps required by prior art systems. Excellent reliability even with an irregular power supply and very low cost are thus assured.

It is an object of the present invention to provide an innovative flow design for a UV water disinfection system, allowing both gravity driven fluid delivery and treatment with a low pressure UV lamp, decreasing energy depletion and environmental impact.

It is a further object of the inventive UV disinfector to provide sanitary water at a low cost and requiring little maintenance thus making safe water available to people in the developing nations.

It is yet a further object of the inventive UV disinfector to provide disinfection of fluids for use in medical, pharmaceutical, food processing, gray water, fish culture, cooling coil drip pan, and research animal colonies.

Due to the many innovative design features of the present invention, a very low energy UV lamp is all that is required to treat large amounts of water, in large part due to the inventive optimized flow design. The carefully designed flow rate and pattern is accomplished with baffles outside of the treatment chamber, angled chamber walls, and specially configured treatment trays and inlet and outflow ports. By relying on gravitational force to power the flow of water, excellent reliability and very low cost are assured, as the pumps required by prior art systems are eliminated.

The innovative UV disinfector has numerous innovative features which provide high quality drinking water at very low cost, about 5¢–7¢ cents per person per year, making safe water available for the first time to many people in developing nations. The availability of a simple, inexpensive method for disinfecting drinking water will save the lives of many people, particularly children who are the most susceptible to diarrheal diseases. Because women are primarily responsible for providing their families with water, the inventive UV disinfection system can greatly improved their quality of life by reducing their workloads and the number of their children lost to waterborne diseases. Apart from the UV lamp and ballast, the device has a life of about 40 years.

The inventive device is also uniquely useful in a large variety of other applications, such as fish farming, portable sanitary units, animal husbandry, disinfection of serum prior to disposal, maintaining water purity in air conditioning systems, etc. The inventive design can be even further simplified for some applications, and tailored to the specific needs of these other uses. For instance, flow rates can be substantially increased in some applications, while certain fail-safe measures are less critical in animal husbandry uses.

The elegant simplicity of the present system provides for very low maintenance requirements, most of which can be accomplished by unskilled users. Additionally, the simplicity of design provides for a light weight, portable system. This allows easy transportation of a unit, even to remote areas. For instance, the unit can be packed in on an animal or animal drawn cart, or even carried by a user in a back-pack. It also allows the sharing of a single unit among multiple water sources, and easy relocation to different seasonal water supplies.

DETAILED DESCRIPTION OF THE INVENTION

Figure 1:
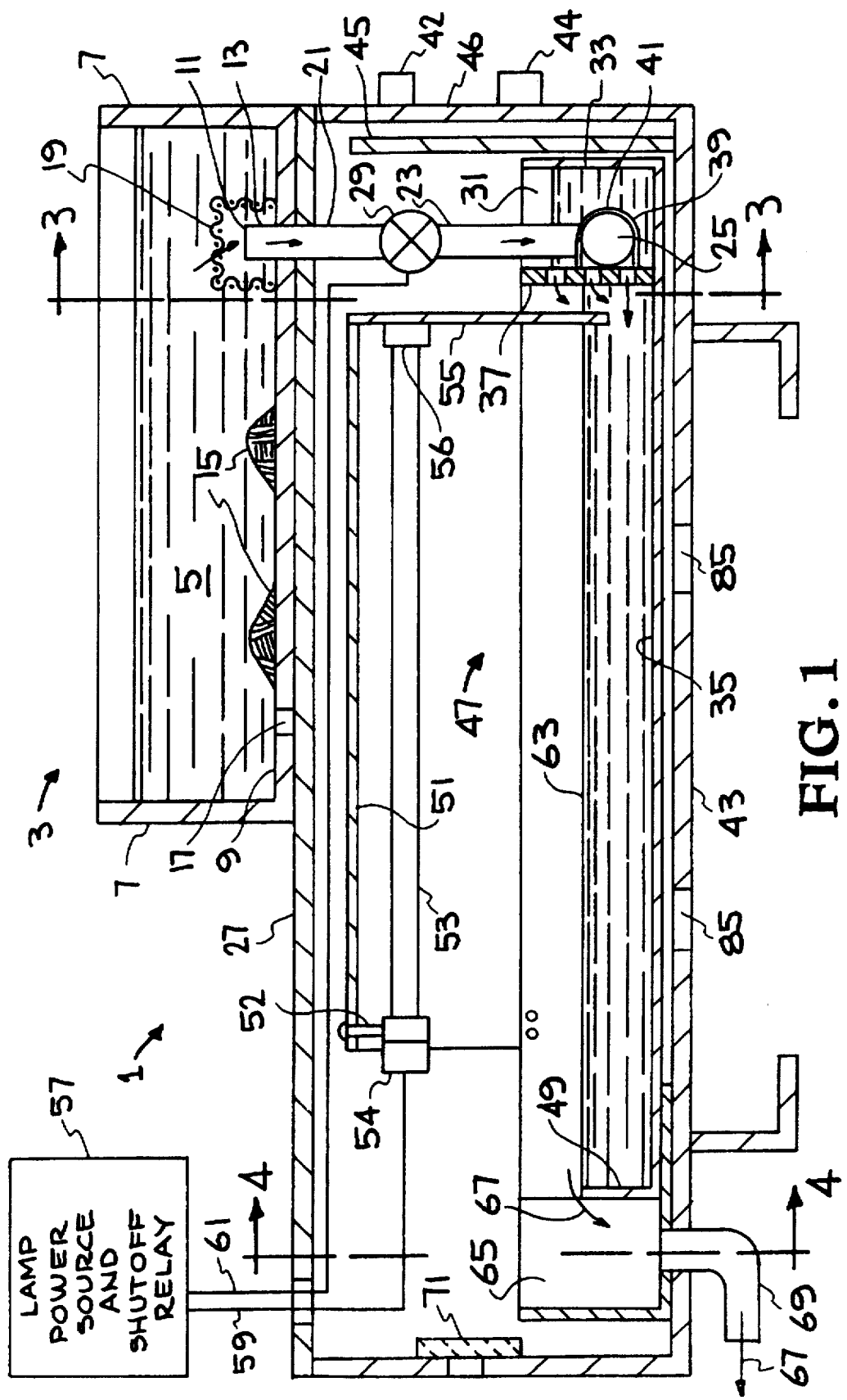
FIG. 1 is a longitudinal view of the inventive UV disinfector.

The integrated UV water disinfection system of the present invention has many innovative features that work in concert to easily and inexpensively produce safe drinking water. There are numerous simple, reliable safety features built into the system which assure that the unit will consistently produce safe drinking water, even under adverse conditions and when employed by unskilled users.

The basic structures of the present device work together to provide a continuous stream of safe water to the user. An entry feed trough directs the feed water into the inlet port of the device. The feed water proceeds into the inlet manifold through a distribution tube. The inventive design of these features causes the water to be of essentially the same pressure throughout the entry chamber. The feed water then enters the treatment chamber through a perforated baffle wall, which laminarizes the flow. Angled sides ensure uniform UV exposure. A UV lamp suspended above the flow treats the feed water, and the pure water cascades over an outlet baffle weir into the outlet manifold and directly into a collection vessel, or into a holding tank from which the water is distributed to the users.

The structure of the entry feed trough provides water to the UV disinfection device at a steady rate which never exceeds the safe disinfection capacity of the unit. The inlet port is calibrated so that excess force of feed water will result in back pressure, resulting in a reduction of flow through the unit. If there is an interruption in power, causing the UV lamp to temporarily cease function, a solenoid operated safety valve in the inlet manifold temporarily blocks the entry of feed water. Other safety features have also been built into the inventive device.

The baffle wall and exit baffle weir fore and aft of the treatment chamber provide for steady, predictable treatment of all portions of the feed water. Angling of the treatment chamber tray, and positioning of the UV lamp and reflectors, assures that even water most distant from the lamp receives close to the same UV dosage as that nearest the lamp.

To assure the safety of the user, the power to the UV lamp cuts off if its protective housing is opened, so that there is no accidental direct exposure to the UV light. While a ground wire is provided to avoid the potential for shock, there is also a Ground Fault Circuit Interrupt (GFCI) provided which will cut off power whenever a short occurs.

Entry Feed Trough

The inventive UV disinfector is typically provided with an entry feed trough fitted to the inlet port at the top of the device. The entry feed trough has a number of functions in the present invention. Among other functions, the entry feed trough provides a reservoir for the feed water, serves as a settling tank, and provides the proper pressure for entry of water into the disinfection device.

The entry feed trough will typically be provided at the treatment site by the users. It can be fabricated out of many standard materials, such as a plastic water drum or large oil drum. These vessel would then be cut to provide a wall which does not go more then ten centimeters above the mouth of the inlet port of the device. When drums are employed, the drum can be cut along a diametrical plane, providing two entry feed troughs which can be joined together to produce a large, long reservoir.

Using bisected cylinders as entry troughs has a number of advantages. They are particularly useful as settling tanks because of the sloped bottom which allows concentration of silt and other debris while minimizing standing water which is not circulating through to the disinfection device. As the solid materials settle out, the silt at the bottom of the trough can be easily scooped out to minimize turbidity problems and provide a better quality drinking product overall.

When two halves of the cylinders are used in a battery, with the connecting portion having a dividing wall of an appropriate height, the first tank will provide an initial settling with the cleaner portion of the water spilling over the dividing wall into the second tank. The second tank, receiving this pre-settled water, will provide an especially low turbidity feed water to the inventive device. This approach would be particularly important when water with high levels of silt or blown earthen dust contaminants is to be treated.

Lifting problems for cleaning and other purposes are minimized by use of bisected cylindrical entry feed troughs. Once disconnected from the device, the bisected cylindrical entry feed troughs can be easily rolled to one side or all the way over for cleaning and emptying. Providing removable props, such as rocks or wooden wedges, to keep the troughs upright during use may be preferable to a permanent stand to allow for ease of cleaning. Alternatively, the half-drums could be provided with a semi-circular cradle stand on which they could be pivoted.

Half-drum entry feed troughs can also be easily overturned for full drying, to avoid catching debris when not in use, and for disinfection or paint drying. It may be useful to periodically roll such troughs onto blocks to allow complete circulation of air on the inner surfaces of the drums.

Using an animal feeding trough, or other flat water holding devices as the entry feed trough would also be appropriate. Because of the large surface area of water exposed, the trough will typically be located in a protected area, or the major part of it covered, such as by a corrugated metal sheet. This will minimize airborne contaminants entering the feed water. Once properly cleaned of residual chemicals, a cement mixing trough could be employed. Such troughs could be lifted at one end for cleaning, and washed or rinsed down to the lower end. If heavy, a fulcrum and lever approach will expedite lifting without undue strain to the user.

The feeding trough may be usefully fitted with a drainage port at the bottom of the trough, although this feature can introduce some leakage problems. By design, there will be a residual water level at the bottom of the trough to provide for settling, so that lifting the trough without complete draining is not a trivial matter. The drainage port is also useful if a permanent mounting stand for the feeding trough is desired. When the drainage port is of a sufficient diameter, the water and silt at the bottom of the trough can be drained simultaneously, perhaps with agitation with a broom or other implement so that the silt remains in suspension during draining.

When space is at a premium, the trough can run the length of the device, typical one meter. However, there are advantages to having the trough run perpendicularly, or otherwise at an angle to the length of the device. For instance, if the device is enclosed in a lean-to or other protective housing, it would be useful to have the water depositing area of the trough in the open or in a higher, perhaps less protected, enclosure. This will allow the user to avoid bending, or otherwise be inconvenienced for providing feed water to the device.

The feed trough serves as a reservoir for the feed water. This is particularly useful when the water is provided in a non-continuous manner, such as when it is retrieved from standing water in bucketfuls, or is provided from a discontinuous source, such as a hand or animal driven pump or variable stream feed. Thus, a user could deposit a relatively large amount of water for treatment, and return at a later time to retrieve the treated water. The entry feed trough also avoids the need for gradual provision of water. For instance, the water can be dumped by bucketfuls, rather than slowly poured. This provides considerably less strain on a user's back.

The entry feed trough aids both in limiting the turbidity of the feed water and providing a rough check of its severity (see below). The UV transmittance of inlet water determines how well the UV light penetrates and disinfects the feed water column. Transmittance decreases with increasing turbidity and dissolved salts. Thus, the entry feed trough provides an excellent opportunity to limit the deleterious effects of turbidity on the overall quality of disinfection provided by the inventive device under highly varying field conditions of use.

The transmittance of the feed water to UV light is quantified as an "extinction coefficient". The larger the extinction coefficient, the faster the UV intensity is extinguished as it travels through the feed water. Feed water with a large extinction coefficient for UV will to some degree protect microorganisms farthest away from the UV light source, potentially compromising inactivation of pathogenes.

The extinction coefficient of pure distilled water for UV is 0.007 $cm^{-1}$. In the present design, it is assumed the inlet water can have an extinction coefficient of 0.3 $cm^{-1}$, which is as large as that of the average water discharged from US waste-water treatment plants. In laboratory experiments, it has been found that the inventive device can disinfect water with turbidities produced by Kaolnite clay of up to 20 NTUs.

Because the inventive device can provide safe water at relatively high turbidity, for everyday use all that will be needed is a crude check for the turbidity of the feed water. Ideally, there will be an initial quantitative determination of feed water turbidity at the installation of the device. This will be followed by periodic back-up testing with a nephalometer to determine a baseline turbidity and provide for periodic monitoring, such as when the lamp is serviced.

The entry feed trough provides an opportunity for an everyday, rough check on feed water turbidity. A small visual pattern can be provided, such as a square with black and white bars, at the end of the trough below the water mark. An observer then positions their eyes at the farthest rim of the trough, and observes the lines to determine if they are distinct. If they are not, the feed water needs to settle until the bars become distinct before processing of the water continues. Regular failure of the rough check would alert the user that a two-chambered entry feed trough needs to be arranged to allow regular pre-settling.

As an alternate turbidity check, a small mirror at a 45° angle below the water mark can be situated at the observer's end of the entry feed trough. The observer would then observe the visual pattern reflected in the mirror thus viewing it through the length of water to observe the bars. This approach would help assure that sufficient water was being intercepted in the line of sight to detect the effect of turbidity. The trough must be at least one meter long in order to provide sufficient data to make a useful check.

Inlet Assembly

The inlet assembly of the present invention includes an inlet port and an inlet manifold which is located in part in the inlet chamber. This pipe assembly will typically be of standard PVC screw together piping, allowing simple disassembly for periodic cleaning or to remove obstructions.

The feed water is delivered into the inlet chamber from the inlet port through an inlet manifold. The inlet manifold typically takes the form of an inverted T, with holes at the lower edge providing even fluid pressure throughout the inlet chamber.

The inlet port of the inventive UV disinfector is provided uphill from and at the end of the device opposite to the outlet port. The inlet port is typically located at the top of the device. The inlet port delivers feed water into the inlet chamber through the inlet manifold prior to water's entry into the treatment chamber. The feed water traverse the port passively by gravitation weight, which dictates the rate of flow into the inlet chamber and the water pressure in that portion of the device.

To maintain the quality of disinfection, it is important that the feed water entering the inlet port is as free of inert material as possible. If sticks, pebbles, leaves, and the like enter the inlet port, they would potentially compromise the effectiveness of the disinfection process. To limit these possibilities, the inlet port is typically fitted with a simple fine mesh screen box. This mesh helps avoid the entry of floating objects into the port, such as twigs and leaves. It also avoids the entry of small animals into the port, such as insects and small rodents. If it becomes clogged, the screen box can be easily wiped clean, or removed and rinsed free of blockage.

Where an entry trough is used, the end of the trough in which the inlet port is situated can be fit with a simple cover, such as an attached piece of wood or metal. This would directly protect the inlet port from the direct entry of inanimate objects, such as flying pebbles or sticks. Such a cover would also serve to avoid the improper forcing of water at an inappropriate rate by dumping directly on the port, or unauthorized attachment of a force pump to the upper entry.

Particularly when no debris screen box or trough end cover are used, it is important that a small lip be provided on the inlet port. This lip can be as little as 3 cm high. Especially with a flat bottom entry trough, the lip avoids deposited silt at the bottom of the trough from being washed directly into the inlet port. It also avoids some eddying and current problems which can occur with splash-back. Because the silt settles on the bottom of the trough, there is less turbidity in the feed water, and problems with baffle clogs and sediment on the internal portions of the disinfection device are minimized.

The diameter of the inlet port is dictated by the design consideration that the maximum height of the column of water (about 10 cm above the top horizontal surface of the cover) in the inlet trough or other entry produces a flow of 15 liters/minute into the inlet port. A different (e.g. smaller) value of the diameter of the inlet port could be provided which would allow a correspondingly different (e.g. larger) height for the inlet trough walls. These values would need to be calculated so as to produce the necessary flow rate useful in the present invention. The parameters which would produce these alternative designs will be obvious to the ordinary skilled artisan familiar with calculating pressure drop during fluid flows through pipes and orifices.

Because the water pressure is necessary to provide the correct treatment of the feed water within the treatment chamber, the level of the water above the inlet port is important. Being solely gravity driven, the flow rate will be dependent on this height and its corresponding pressure. Providing an entry feed trough whose capacity can not reach more than ten centimeters above the inlet port [or other heights as described above] provides a natural means of limiting the pressure of the water which is presented to the inlet chamber from the inlet port.

By providing a feed trough with appropriate wall height if a user pours water too rapidly into the feed trough, the feed trough will simply overflow. This helps assure proper pressure levels in the inlet manifold. Provision of an entry feed trough can also limit the tendency of an impatient user to attempt to force water through at an incorrect rate, as the trough provides a reservoir so that other activities can occur while the water is being processed.

Communities with a pressurized piped supply of unsafe water could feed the trough through a simple float valve to ensure a continuous supply of disinfected water into another (holding) tank, from which the community could be supplied.

The use of a feed trough attached to the inlet port can also help avoid incorrect pressure in the device. In many communities in which the device is in continuous use, feed water can be deposited by the immediate user into the feed trough for eventual processing, but a like amount of treated water immediately retrieved from the community reservoir of treated water. Thus, providing a reasonable size of reservoir for treated water may avert the user's temptation to force an inappropriate rate of feed water into the device, while providing "instantaneous" treatment.

In some uses of the inventive disinfection device, the feed water will be introduced into the inlet chamber from below by a hand pump. The device can directly form the spigot section of the pump. In this case, the water enters the device from below and its rate will be determined by the hand pump design and pumping effort applied. In this embodiment of the invention the inlet manifold can be much larger without any detrimental performance. However, it cannot be much smaller than upper entry applications since a smaller inlet manifold will generate more back pressure which must be overcome before the flow can proceed through.

A safety device below the inlet port within the inlet manifold can be provided which stops the flow of feed water into the inventive device whenever the electrical flow to the lamp is interrupted. Such interruptions of electricity can occur when there are shorts to the circuit or a battery runs low. This can also occur if the power source is of a type which provides power irregularly, such as a photovoltaic array, a small hydroelectric source or a typical rural power grid in a developing country. In one embodiment of the invention a solenoid is provided at the inlet tube which, when the power supply is interrupted, snaps a circular wafer into place, or closes a butterfly valve.

Inlet Chamber

The feed water enters an inlet chamber from the inlet port attached through the inverted T shaped inlet manifold housed in part in the inlet chamber. A constant fluid pressure throughout the inlet chamber is maintained during the processing of feed water by the height of the water column and the positioning of the bores in the distribution tube. These factors control the force and flow of water entry into the treatment chamber. This constant pressure is necessary so that the baffle wall described below can effectively laminarize the flow of feed water through the treatment chamber.

The water enters the inlet chamber through a distribution tube portion of the inlet manifold, at its distal end, which runs parallel to the baffle wall. The distribution tube is fed from a vertical inlet tube portion of the inlet manifold, and extends from this tube horizontally on either side in an inverted T configuration. The distribution tube is typically submerged near the bottom of the inlet chamber, and is provided with exit holes. These holes can be directed at the back of the inlet chamber or at the baffle wall without ill effect. In one embodiment, the distribution tube is attached to the baffle wall. While some shadowing of the laminarization occurs in this configuration, the feed water is still effectively treated and eddying and varying pressure in the outlet chamber is minimized.

When a wide disinfection device is provided, such as when greater capacity is required, the holes in the distribution tube, which are positioned farther from the vertical inlet tube and approach the sides of the inlet chamber, are provided with a larger radius. This configuration provides a consistent pressure of water within the inlet chamber from wall to wall, and assures correct laminarization of the feed water flow through the treatment chamber. Specific dimensions of these holes to provide the equal pressure at a required level throughout the inlet chamber can be ascertained for any particular configuration by the ordinary skilled artisan from standard hydraulic flow and pressure tables.

Baffle Wall

A baffle wall separates the inlet chamber and treatment chamber. This inventive feature, in concert with the outlet baffle described below, produce a unique hydrodynamically optimized system for delivering feed water to be treated by UV light. It also serves as an additional reflector to redirect UV light towards the feed water, providing a higher net dosage to the feed water.

The inventive baffle wall is provided with cutouts which laminarize the flow of water from the inlet chamber into the treatment chamber and restrict the water flow to maintain the optimal level of water in the treatment chamber. These functions of the baffle wall provide an optimal flow rate and quality during the treatment process.

In prior art technology, the use of baffles often introduced safety problems because they produced a UV light shadowing effect during treatment. This phenomena left certain portions of the feed water under treated, and brought the safety of the product into question. This design problem has been eliminated in the present invention by locating the baffle wall outside of the treating chamber, so that shadowing problems are eliminated entirely.

Because of the consistent laminarized flow of water produced by the baffle wall, the production of eddies or other irregularities of feed water flow is limited or eliminated all together. This function of the baffles is critical to providing treatment at a low cost, dramatically minimizing the level of UV light production required to provide safe drinking water. On the other hand, in prior art technology multiple baffles within the treatment chamber produce eddies causing an undesirable wide distribution of UV dose to the water being treated.

The spacing and diameter of the holes in the inlet baffle wall are designed to re-laminarize the flow from the inlet port and manifold into the main treatment tray. If the total area of the holes is changed significantly, it would interfere with the flow pattern necessary for appropriate treatment of the feed water. The proportion of hole surface to solid surface in the baffle wall can range from 10% to 30%. A more preferred range is from 12% to 20%. A most preferred percentage is 15%.

Other factors beyond mere percentage of outlet hole area in the baffle wall are considered in designing an appropriate baffle configuration. If there are a low number of relatively large holes provided in the baffle wall, there occurs the risk that the outgoing flow from the inlet chamber will contain too much turbulent energy to provide appropriate laminar flow. Conversely, if a very large number of unduly small holes are provided, there is the risk that they may become clogged by small debris that may enter the inlet. Such clogging would compromise the laminar flow provided and put at risk the effectiveness of the water treatment. An ordinary skilled artisan will be well equipped to balance these factors when providing different embodiments of the present invention.

A reflective wall is provided just downstream of the baffle wall. The reflective wall extends from the roof of the treatment chamber to just below the top of the baffle wall typically a flat sheet directly abutting the end of the curved top reflector. This reflective wall serves to avoid surface perturbation of the feed water flow into the treatment chamber, as well as skims off any floating debris that may enter the inlet chamber.

Treatment Chamber

The treatment chamber provides the regulated flow of feed water beneath the treating UV lamp in order to produce biologically decontaminated water. The chamber has several features to assure that this critical flow of water is achieved. The baffle wall, in concert with the maintenance of steady water pressure throughout the inlet chamber, provides for consistent laminar flow of the feed water in and through the treatment chamber. The reflective wall avoids surface perturbation and eddying. Angled treatment chamber walls physically position the water so that it receives a narrow distribution of UV dose.

The UV lamp which overhangs the feed water stream at a carefully determined height from the treatment chamber floor provides steady, direct treatment of the water. This inventive design avoids prior art quartz sleeve problems of bio-deposits, mineral deposits and other UV light obstructing materials. The lamp is provided with a curved reflector, which serves as the ceiling of the treatment chamber. This allows the recapture of UV light directed towards the ceiling facing surface of the lamp, and redirects it to the feed water stream. Advantageously, this secondary UV light is generally directed towards the feed water stream closest to the walls of the chamber. This inventive configuration provides extra exposure to a portion of the stream otherwise receiving less dosage than that more centrally located.

The baffle wall in concert with the entry manifold provides the entry of the feed water into the treatment chamber in parallel, liner laminarized flow at a steady state and pressure. While slowing or stoppage of flow from any one of these holes would change the dynamics of the flow to a certain degree, the system can tolerate a certain percentage of compromised flow without effecting water quality due to the reorienting effects of adjacent laminarized flow streams. Periodic maintenance and cleaning of the inventive UV disinfectors will assure the quality of the disinfection. Usage and feed water quality will dictate the period between maintenance visits. In unusual circumstances where biocontaminates are particularly severe, user testing can be done between standard maintenance visits. A simple test to observe occlusion of the perforations is typically done with a food color aliquate, as described in the "observation window" section below. Increasing the flow rate by tipping the disinfector well above the correct treatment level can serve to clear the occlusion.

Angled walls in the treatment chamber serve to generally focus and direct the laminarized flow. Additionally, by effectively positioning all water within a specific distance from the lamp, the predictable treatment of all water by a specific dosage of UV light is assured, obviating under treatment of portions of the feed water which might otherwise result due to the decrease in UV intensity by geometrical factors and the extinction coefficient of the feed water. This special feature of the invention allows inexpensive, low-pressure UV lamps to be used to treat large volumes of feed water.

The slopes of the wall beveling of the present invention were calculated in order to position the water to at all times be at a certain minimal distance from the UV lamp. This radiometrically optimized designed also provides that the angles of the walls are coordinated with the lamp reflector panels to optimize each portion of the feed water's exposure to UV light. The design provided by the present invention actually provides for exposure of the water at the farthest walls of the treatment chamber at very close to that received by water closely positioned to the UV lamp. These features of the invention are central to providing a low cost, efficient disinfection system.

Residence time of the water, as well as water depth, are also closely regulated in the treatment chamber to provided maximum, nearly homogeneous exposure of the feed water at the most minimal possible cost. The depth of the water is greatest nearest the lamp, and is gradually tapered to a shallower level at greater distances from the lamp. This ensures a very narrow and efficient distribution of UV exposure through the volume of water because the extinction of UV light is considerably less in shallow water.

Additionally, water adjacent to the walls of the device and near its bottom surface will flow at a slower rate due to the effect of friction. This phenomenon provides a longer residence time in the treatment chamber for those portions of the feed water most distant and most shielded by other water from the UV lamp. In this way, the innovative design of the invention normalized the difference in UV water exposure in different sections of the treatment chamber to create a narrow and effective system to disinfect water with UV light.

One potential problem with any UV disinfection system is that feed water may somehow be forced through the system at a rate greater than that at which it can effectively treated. This is less of a problem in the present system compared to others, as the certitude of gravitational force is relied upon to provide the appropriate flow. However, improper leveling, attaching a pump improperly providing a forced flow, or substituting a deep vessel for the inlet trough could potentially overload the disinfection device. As a first means of avoiding inappropriate water pressure, the inlet port is of a controlled size, so that the flow of feed water will experience a back pressure if it is of too high a rate.

A special design feature of the inlet chamber tray walls avoids inappropriate height of water in the treatment chamber is also provided. In addition to avoiding incomplete processing, the water level in the treatment chamber must be controlled to avoid damaging the lamp, shorting out the electrical systems, as well as electrical safety considerations to the user. The treatment chamber is designed in an open configuration with walls of a specified height. The enclosure housing the exposure chamber is also provided with bottom slots so that overflow from the walls during improper forcing will be directed away from the device, and drain quickly away to avoid any water damage.

One embodiment of the present invention can treat a maximum throughput of 15liters per minute. If a larger flow is forced into the inlet port, the excess water overflows the treatment chamber tray walls or exits through evacuation cutouts on the tray walls. This excess water flow is then directed out of the device from the bottom slots in the device. These slots are specifically provided so that the excess water does not flood the internal workings of the device, exit untreated from the outlet spout, or cause electrical shorts.

UV Lamp and Electrical Source

The innovative design of the present invention allows the use of a standard, low cost UV lamp. The lamp is positioned above the flow of water at a specific height above the floor of the treatment tray. This innovative positioning eliminates the need for expensive quartz or Teflon sleeves, and means for cleaning them, currently required by UV disinfection devices. The specific height above the floor of the treatment tray is critical to appropriate radiometric dosage of the feed water. Because of its simplicity, and several innovative safety features, the present invention can be powered from virtually any electrical source. For instance, in isolated areas, only a small photovoltaic panel would be required to run the inventive device. Small hydroelectric devices or wind turbine-generators can also provide sufficient power to run the inventive disinfector device. When the device is powered from irregular, rural main power sources, a shutoff relay would be required to cut off water at the inlet port during periods when the power is interrupted. This feature of a safety shut off valve is described in the inlet port section above.

The inventive device can be powered with a car battery using a trickle charge to avoid the safety problems and inconvenience to the user which can occur with an irregular power supply. Since the simple and efficient design of the present invention results in very low power requirements, a simple 12-volt car battery can be used for the necessary power requirements. This power source is particularly useful in communities, such as villages, where the power supply is intermittent. The battery can be recharged when the main source of electricity is available. This approach would allow processing at night if the battery is used as a storage unit for electricity produced by photovoltaic arrays, irregular waterwheel power, or other sources which suffer from power-outages.

A splash proof On/Off switch is ideal for use in the present invention. Many companies make such gasketted switches, such as Mulberry. The 30480 Mulberry switch comes with a switch, gasket and splash-proof cover.

Any use of electricity in association with flowing water presents the potential for electric shock to the user. In order to avoid this problem, the circuitry of the present device is with a Ground Fault Circuit Interrupt. This is provided at the power source of the unit, and is particularly important when 120 VAC or 230 VAC supply is used. Whenever the system is shorted, there is an immediate disconnect of the power. A 2 amp fuse is also provided between the On/Off switch and the ballast.

A simple grounding wire avoids the potential for shocks. Any electrical leak to the body of the inventive device thus gets grounded, and cannot cause an electrical shock to a person touching the device. The power cord should be protected from chaffing at the metal edge of the entry hole where it enters the base. Use of a rubber gasket at the entry hole for the power cord is one means of preventing this problem. Additionally, a knot is tied in the power cord or with the three strands of the power cord just inside the entry hold. This knot prevents a mechanical pull on the outside cord from being transmitted to its electrical contacts inside the unit.

Safety labels in the local language near the electrical cord entry are listed as "CAUTION: Intense UV light inside the unit CAUTION: Do not open unit without first disconnecting power supply".

A safety consideration in any use of UV lamps is that unmodified UV light is potentially dangerous to the user, such as by observing it with the naked eye, etc. The present invention is so provided that if there is any disassembling of the protective casing around the lamp or its housing, the electrical power to the lamp shuts off. The treatment chamber's interlock system eliminates the risk to systems operators of accidental exposure to the UV light.

In the inventive device, the UV lamp is the component with the shortest life. One typical lamp in one embodiment of the invention has 8000 burning hours. When the lamp goes out, or there is any malfunction that interferes with the lamp operation, the users can observe this status immediately through the safe viewing window described below. Depending on the daily hours of use, the lamp can be replaced routinely once a year if it is used an average of 20 hours a day, or once every 2 years for units used an average of 10 hours a day. An optional feature is a circuit that switches on the germicidal UV lamp when water is introduced to the inlet and switches it off three minutes after water is no longer entering the inlet (the residence time of water in the device is only about 12 seconds). This can save electricity and also substantially prolong the life of the electronics and the UV lamp.

Routine cleaning and inspection of the lamp should occur every six months just to ensure smooth operation year round. The lamp would then normally be replaced during alternate or every forth cleaning and inspection runs. In some communities, this will happen when a maintenance worker comes through the village on a periodic schedule. Laminarization testing with a food-color aliquate and turbidity sample collection would normally occur at the same time.

The electronic ballast is the other component of the inventive device with a limited life span. It typically is rated at 20,000 burning hours. Typical commercial ballasts suitable for use in the present invention would be for 120 volt AC supply a Motorola Electronic ballast No. MI-RN-T12-ILL-120.

View Window

The safety view window allows the direct observation of the UV light to determine its function. Located in the front plate of the base described below, the window is made of a material opaque to UV light, allowing the direct observation of the light's status with the naked eye without any risk to the observer. In one embodiment of the present invention, the window is constructed of 4 mm thick polycarbonate, meeting the criteria of allowing observation of the light which being essentially opaque to ill effects to the viewer. It is attached to the inside surface of the housing by four screws. Near the view window should be the following label in the local language "NOTE: The unit is not working unless blue glow shows through the window". One can also provide international symbols when some users may be illiterate.

The inventive feature of a view window provides a quick check to directly observe if the UV source is on, or if it is being in some way compromised, such as by bio-deposits on its surface. It is important that the light be checked at the time that a run of water is taken from the device to establish that the bulb has not blown out. However, the light need not be observed continuously during processing, even in situations with a discontinuous electrical source. This is because a fail-safe stop-cock on a solenoid circuit is provided as above which will block the flow of water into the device whenever there is a break in the power supply. Use of a car battery as a source provides an extra measure of certitude of availability in this regard, because the time of use of the device need not be correlated in any way with the time of availability of grid electricity to charge the battery.

The view window also provides an opportunity to periodically test the laminar flow of the feed water from the inlet chamber into the treatment chamber. A small amount of liquid food color dye is added as an observable aliquot to the inlet port. The observer then notes if the laminar flow is maintained through the treatment chamber by observing the new colored laminar streams. Small blockages in the baffle wall can then be observed directly, and normal maintenance steps taken to restore the flow if it is compromised.

Outlet Baffle and Port

The outlet baffle takes the form of a shallow weir at the downstream end of the treatment chamber. The treated water rises to the necessary level, and then cascades over this blockage into an outlet tray. In the embodiment of the invention illustrated in FIG. 1, the baffle is 5 cm in height as compared to the 10 cm overall height of the main tray. The treated water then proceeds from the outlet tray through a tube to the outlet port, where it can be made directly available to the user, or can be directed into a safe water holding tank. The outlet port is provided 2.5 cm above the base of the tray, both to provide for structural stability, and to provide one last settling area prior to the distribution of treated water. A drainage plug can be provided to clear this area without resort to disassembly of the unit.

The treated water is delivered through a spigot to the user, or can be channeled into a storage tank, as provided below.

Because the system disinfects approximately 30 liters of water a minute, a very reasonable flow of water is provided by the device. By comparison, this rate exceeds the flow from a typical U.S. bathtub faucet or common garden hose.

Safe Water Holding Tank

As described above, having a holding tank of sufficient volume, and a large feed trough, can provide the user with "instant" processing. If there is a community holding tank, after an initial start up introduction of feed water, each new user takes from the holding tank the amount of feed water they introduce, allowing the feed water to run in its own time. Such a holding tank would of necessity have to be protected against introduction of contaminates. Ideally, the safe water holding tank would be a sealed tank with a spigot outlet in order to provide for this quality.

Typically, narrow necked vessels are used to transport the safe water product of the present invention to homes for household use. Narrow necked vessels, ideally with stoppers, will help assure that the safe water does not get contaminated from any contaminated hands or pots dipped into it. Narrow necked vessels also help guard against loss of water during transport due to splashing. Polyethylene jerry cans of this type are low cost and rugged, and add little weight to the heavy load of water. Ideally, dollies can be used to minimize the effort needed by the user to transport the water home, especially with ill or elderly users.

Housing

The housing of the present invention allows both low weight characteristics to provide easy portability, but also a rugged character resulting in long life of the unit. It can be constructed of stainless steel to provide increased structural stability and resistance to corrosion. By contrast, portions of the device which are not in contact with water, and which face on the interior of the treatment chamber are preferably of polished or buffed aluminum, as the reflective nature of the aluminum increases the exposure of the water to UV.

By providing folded metal for much of the unit, welding joints are minimized, providing for limited problems of leakage. When joints have contact with the water stream, they are typically sealed with a silicon epoxy sealant. Joints exposed to UV light can be additionally sealed with stainless steel tape to avoid the possibility of silicon epoxy breakdown due to UV exposure.

Where air-born contaminates are a problem, the housing can be fitted with a simple air filter. This allows regular circulation of air about the UV lamp to avoid fogging or biomass buildup, without risking contamination from airborne particles. However, the working temperature of the lamp typically avoids such complications. Problems of introduction of pathogenic spores or general dust causing turbidity problems or fouling would be minimized by minimizing air circulation through the unit.

The housing consists of the cover unit which, when fit into the base, fully encloses the core assembly. The base frame is constructed of aluminum angle beam, and attaches to the inside surface of the base. The base frame provides the framework for assembly of the cover and core assembly to the base, and provides stability to the core assembly and the unit as a whole.

Where there are joints in critical areas, the unit should be sealed. This provides both a continuous conduit of the inlet water and treated water, and also minimizes both water and airborne contaminants. Commercial silicone metal glue sealants such as "Silicone II Metal Glue & Seal" by GE Silicones or "2084 Metal Sealant" made by Scotch-Seal are examples of such suitable sealants.

Installation and Correct Alignment

The present invention is generally tough and durable. However, it is likely that the inventive device will be used under at times extremely harsh conditions, such as high heat and humidity, heavy rains, very cold temperatures, etc. To extend the life of the device and achieve its optimal functioning, its instillation and care should be given attention.

In harsh climates, a simple housing such as a lean-to will help prolong the life of the device, and limit the introduction of particulate and other materials (including pathogens and insects) into either the feed water or the pure water product. This will limit the amount of maintenance required to keep the interior of the device free of deposits. As explained previously, the device can be housed separately from the entry feed trough as well as from the pure water holding tank.

When housing is not desired or is impractical, it can be useful to situate the device near some protection from the elements, such as under a tree, near a bluff, in the shade of a home, etc. A corrugated aluminum sheet, or other roofing can be used to shelter the device. If the device is located near a well, it is likely there is a preexisting shelter that can commonly protect both the well and the device. In more affluent communities, individual devices can be located directly in the home. This provides maximum protection for the device, and limits potential post-treatment introduced contaminants.

It is generally preferable that the device be kept some height above the ground. This positioning will avoid a high concentration of dust and debris that is regularly made airborne directly above the ground. Such positioning also limits insect and other animal invasion of the device. Maintenance and safety checks are better accomplished when the device is kept in a raised position, for instance on a platform. In one embodiment of the invention, the device is provided with short legs to provide some clearance with the ground.

Elevated installation of the inventive device is particularly important in communities which have periodic flooding, such as the monsoon season in India and other neighboring countries. During this time, heavy rainfall can wash raw sewage and other contaminated material from the fields into the wells and surface water. Because this poses an immediate health threat to villagers from cholera and other water born disease, safe function of the inventive unit becomes particularly critical. Elevated placement of the device can limit or eliminate contamination of this one safe source of water by water-born pathogens.

The device needs to be kept level during water treatment to allow appropriate treatment of the feed water. Typically, the device will be positioned on a cement slab, or rock surface. Additional leveling can be accomplished with shims. This placement limits the potential for vibration during treatment which could potentially compromise the laminar flow. In one embodiment of the invention, leveling legs are provided on the housing which allows alignment of the device to the horizontal using leveling screws.

In order to assure leveling, two bubble levels are provided which are permanently attached on the exterior of the housing. One of these will be situated in the line of pitch, while the other is in the line of yaw. When the device is so positioned that the bubbles in each level fall within the level lines, the device is positioned for optimal function. These levels will need to be checked periodically to assure that settling, jarring, or other activities have not caused the device to go off level.

The flow rate of water during periodic flushing can be increased by tipping the device higher at the inlet end purposely positioning the device off level. By exceeding the treatment flow rate, eddying, backflow, and increased feed current will stir up sediments deposited inside the device. These are then flushed out of the system prior to its being returned to service. The device can be tipped in the reverse direction to dislodge biomass occlusion of baffel wall perforations.

There are a number of advantages that accrue from the portability of the present invention. The unit can be easily transported to remote areas by simple means, such as by pack-animal or even by a user in a back-pack. The unit is durable enough to withstand the jarring of an ox drawn cart or jeep on a rough road.

The portability of the unit can also be used to provide purification at several water sites in a local area. A movable platform can be helpful for this type of local relocation, such as a cart with retractable wheels or pallet with handles. In this way, the unit can be used to serve an entire village. The design allows for serial placement at different water sources to avoid the taxing process of physically carrying water from its original source to a processing area, and back to the place of use.

Other Applications

The embodiment of the present invention typified in the figures and in Example 1 is directed to providing high-quality drinking water to people in rural areas and developing nations. However, the elegantly simple inventive disinfection device can be effectively and often uniquely used in many diverse applications.

There are important medical applications for the present invention. In developing nations, a reliable source of sterile water is typically not available to clinics and pharmacies. However, there is a need for safe water for such purposes as washing the clinicians' hands, irrigating and cleaning wounds, mixing pharmaceutical preparations, etc. In such uses as wound irrigation and pharmaceutical preparation, residence time may be slowed or water provided with multiple treatment in order to assure near sterility of the water. Small, narrow necked vials for storage and transport of the water are preferable.

Effluent from in-field sanitary devices needs to be treated before being reintroduced into the environment in order to avoid contamination of the surface or ground water with coliform or other bacteria. This water is comparable to the "gray water" which is produced by waste treatment plants. In these small, in-field units, the effluent approaches 500 gallons a day. This effluent, when treatment is adjusted for extinction coefficient, can easily be treated by the present device to provide for safe return into the environment.

Intensive fish culture is developing into a very important part of agriculture as over fishing decreases natural fish stocks. In culturing such fish as salmon, there is a continuous flow of water through the school, allowing the animals to swim continuously. However, this continuous water flow, containing food and elimination products, can quickly develop high levels of bacterial contaminates.

The continuous flow of such fish culture systems provides a good match for the present invention. The inventive device would be put in a small diverted stream which would run continuously with the larger culture stream. Because the goal would be to consistently lower, rather than eliminate, the bacterial growth, the flow rate for the device would be considerably increased. That is, the fastest flow rate which would allow about an 80% reduction in bacterial levels in the feed water would likely provide an optimal treatment approach. The goal would be to kill as many bacteria grossly in the shortest period of time, as the "pure" water would be immediately returned to the original culture water.

Disinfection of biohazardous liquids is also efficiently accomplished with the inventive device. For instance, it is difficult to disinfect high volumes of serum used in producing vaccines to dangerous pathogens. Many of these waste products contain viral contaminates which are potentially extremely virulent. The inventive device very effectively neutralizes this risk.

Drain pans in large cooling devices, such as cooling towers or large scale air conditioning systems, are susceptible to development of pathogens and their wide-scaled dissemination. The legionnaires disease problem is a case in point, where this deadly disease was spread through an air conditioning system in a hotel. There are problems with development of biomasses on cooling tower devices used in heavy industry. The inventive device's compact body and high throughput rate makes it an ideal solution to such challenges.

Another well tailored application for the inventive device is in providing aseptic water for research animal colonies which are kept in aseptic conditions. For instance, feed water could be taken from the municipal water supply. Because treatment is continuous, the animals would have a constantly fresh supply of drinking water. This would be a substantial improvement over current methods of using expensive distilled water.

FIG. 1 provides a longitudinal view of the inventive UV disinfector 1. Atop UV disinfector 1 rests inlet trough 3 typically one meter in length. Feed water 5 is limited in height to 10 cm by the inlet trough walls 7 which do not rise above that height, measured from the inlet trough floor 9. Because inlet trough 3 is typically provided with only a partial covering if any, the inlet trough walls 7 effectively limit the height of the feed water 5. This feature provides an upper limit to the water column weight above the UV disinfector 1, assuring that the correct rate of gravity driven flow of feed water 5 for appropriate UV treatment is never exceeded.

The inlet port 11 (about 1½ cm in diameter) typically protrudes into the inlet trough 3 through the inlet trough floor 9. An inlet port lip 13 extends upwards of the inlet trough floor 9, typically by 2 to 3 cms. When the feed water 5 is carrying insoluble particulates, some portion of these materials will naturally settle on the inlet trough floor 9 as inlet trough sediments 15. When the feed water 5 is washed into the inlet trough 3, such inlet trough sediments 15 can remix with the feed water 5, potentially compromising the UV treatment of the feed water 5, and some portion deposit within the UV disinfector 1, which can limit the reflectivity of internal surfaces. The provision of inlet port lip 13 mitigates against this possibility. Between treatment sessions, inlet trough sediments 15 can be cleaned or wiped from the inlet trough floor 9. The inlet trough floor 9 is optionally provided with an inlet trough drain 17 which is plugged during treatment sessions, but can be opened to expedite cleaning of the inlet trough 3 by allowing a wash-though of accumulated inlet trough sediments 15. The inlet port 11 is further provided with an inlet port screen 19, in the form of a box, which excludes larger particulates, such as small sticks and stones, or floating leaves, from entering inlet port 11 and potentially compromising the efficacy of the UV disinfector 1. The inlet port screen 19 also serves as a deterrent to an impatient user attempting to force water at an inappropriate rate by attaching a force pump to inlet port 11.

The feed water 5 enters the UV disinfector 1 through the inlet port 11 by gravitational force. The height of the inlet trough walls 7 and the diameter of the inlet port 11 are so selected to provide a through-put rate of feed water 5 at about four gallons per minute. The inlet port 11 enters an inlet manifold 21, which is comprised of a vertical inlet feed tube 23 (about 16 cm in length) which connects to a horizontal inlet distribution tube 25 (about 21 cm in length). Thus, the inlet manifold 21 forms an inverted T configuration. The inlet feed tube 23 enters the UV disinfector 1 from above, traversing the outer casing lid 27 through a hole. Provided in the inlet feed tube 23 is a solenoid shut off valve 29 which will stop the flow of feed water 5 in to the UV disinfector 1 if there is a stoppage of power to the UV disinfector 1.

The bulk of the inlet manifold 21 is situated in the inlet chamber 31. The inlet chamber 31 is defined by the main tray inlet wall 33 (about 30 cm by 8 cm), the main tray floor 35, and the baffle wall 37 (about 20 cm by 8 cm). There is about a 7 cm separation between the main tray inlet wall and the baffle wall 37. The inlet feed tube 23 typically abuts the baffle wall 37. The inlet distribution tube 25 typically rests directly on the beveled sides of main tray floor 35, providing for considerable stability. Additionally, the inlet distribution tube 25 is typically attached to the baffle wall 37 by ring attachments 39. The distribution tube 25 is provided with distribution tube holes 41, which provide a flow-through of feed water 5 into inlet chamber 31. The size and positioning of the distribution tube holes 41 provide that the pressure of the feed water 5 in the inlet chamber 31 is relatively constant.

Regulation of water pressure entering the UV disinfector 1 is provided by having a water column of a specific height in the inlet trough 3 by limiting the height of inlet trough walls 7, and by limiting the inlet feed water flow by restricting the diameter of the inlet port 11. If these safety features are somehow circumvented, the main tray inlet wall 33 and the sides connecting main tray inlet wall 33 and baffle wall 37, which are not seen in this view, are provided at a limited height so that the feed water 5 will overflow these walls, primarily the side walls. This excess feed water 5 falls to the outer casing bottom 43, where it drains away through the usual gap which occurs at the juncture of the outer casing top 27 and the outer casing bottom 43.

As a secondary spillage area, excess feed water 5 can spill over the secondary drain main tray inlet wall 33, the excess feed water 5 collecting in the space formed by the main tray wall 33 and the inlet splash plate 45 (about 16 cm by 30 cm) where it will, as when it spills over the sides connecting the main tray inlet wall 33 and the baffle wall 37, drain away through the usual gap which occurs at the juncture of the outer casing top 27 and the outer casing bottom 43. When this occurs, the inlet splash plate 45 protects the electrical connections which are housed behind it.

The inlet splash plate 45 is positioned parallel to the end of the outer casing inlet end 46 which is formed where outer casing base 43 extends upwards at the inlet end of UV disinfector 1. The outer casing inlet end 46 is fitted with fuse 42 and switch 44.

Treatment chamber 47 is defined by baffle wall 37, main tray floor 35, outlet baffle dam 49 (about 30 cm by 4 cm), and curved top reflector 51 (42 cm circumferentially, 30 cm diameter by 42 cm) the later two being spaced longitudinally about 4 cm apart. The curved top reflector 51 houses the UV lamp 53 which is seated in socket 54. Socket 54, in turn, is attached to the curved top reflector 51 by socket attachment bolts 52. Thus, the curved top reflector 51 supports and suspends the UV lamp 53 above the treatment chamber 47. Additionally, the end reflector 55 is fitted with a UV lamp support clip 56 which supports the UV lamp 53 at the end closest to the inlet chamber 31. The central axis of UV lamp 53 is positioned 8 cm above the main tray floor 35 and 7 cm below the curved top reflector 51.

Power source and shut off relay 57 provides the power to UV lamp 53 through lamp circuit 59 and the ballast, not shown in this view. The power source and shut off relay 57 is additionally connected to the solenoid shutoff valve 29 through solenoid wire 62.

At the inlet end of the device, the curved top reflector 51 is abutted by end reflector 55 which is about 30 cm by 13 cm. The end reflector 55 extends downwards past the top of and parallel to baffle wall 37, with its lower edge typically resting below the surface of the feed water 5 that is passing through the treatment chamber 47. There is a gap of about 2.5 cm between the end reflector 55 and the baffle wall 37.

The main tray floor 35 rests directly on the outer casing base 43. The main tray floor 35 is angled to direct the laminar flow 63 of the feed water 5 which is produced by the baffle weir 37. This angling is shown and described in later figures. By constructing all but the ends of the main tray (not shown in this figure) of a single sheet of metal, excellent structural stability and minimal joints are achieved.

The curvature of curved top reflector 51 recaptures otherwise lost UV light from the top of UV lamp 53, directing it back to the laminar flow 63. The feed water 5 traverses the treatment chamber 47, and then cascades over outlet baffle weir 49. Working in concert, these various features of the treatment chamber 47 provide that the feed water 5 directed in the laminar flow 63 typically receive a similar dosage of UV radiation wherever it is positioned in the treatment chamber 47.

The outlet box 65 receives the treated water 67 as it cascades over the outlet baffle 49 which is about 5.5 cm from the back wall of outlet box 65. The base of the outlet box 65 slips beneath the main tray floor 35 by about 7 cm and above the outer casing base 43. The outlet box 65 is provided with an outlet port 69 (about 2.5 cm in diameter) through which the treated water 67 flows out of the UV disinfector 1.

The end wall of the outer casing lid 27 next to the outlet box 65 is provided with a view window 71 about 5.5 cm in diameter. This is made of a material which will protect a user viewing the on-off status of the UV lamp 53 from eye damage. It is secured to the outlet casing lid with four screws.

Figure 2:
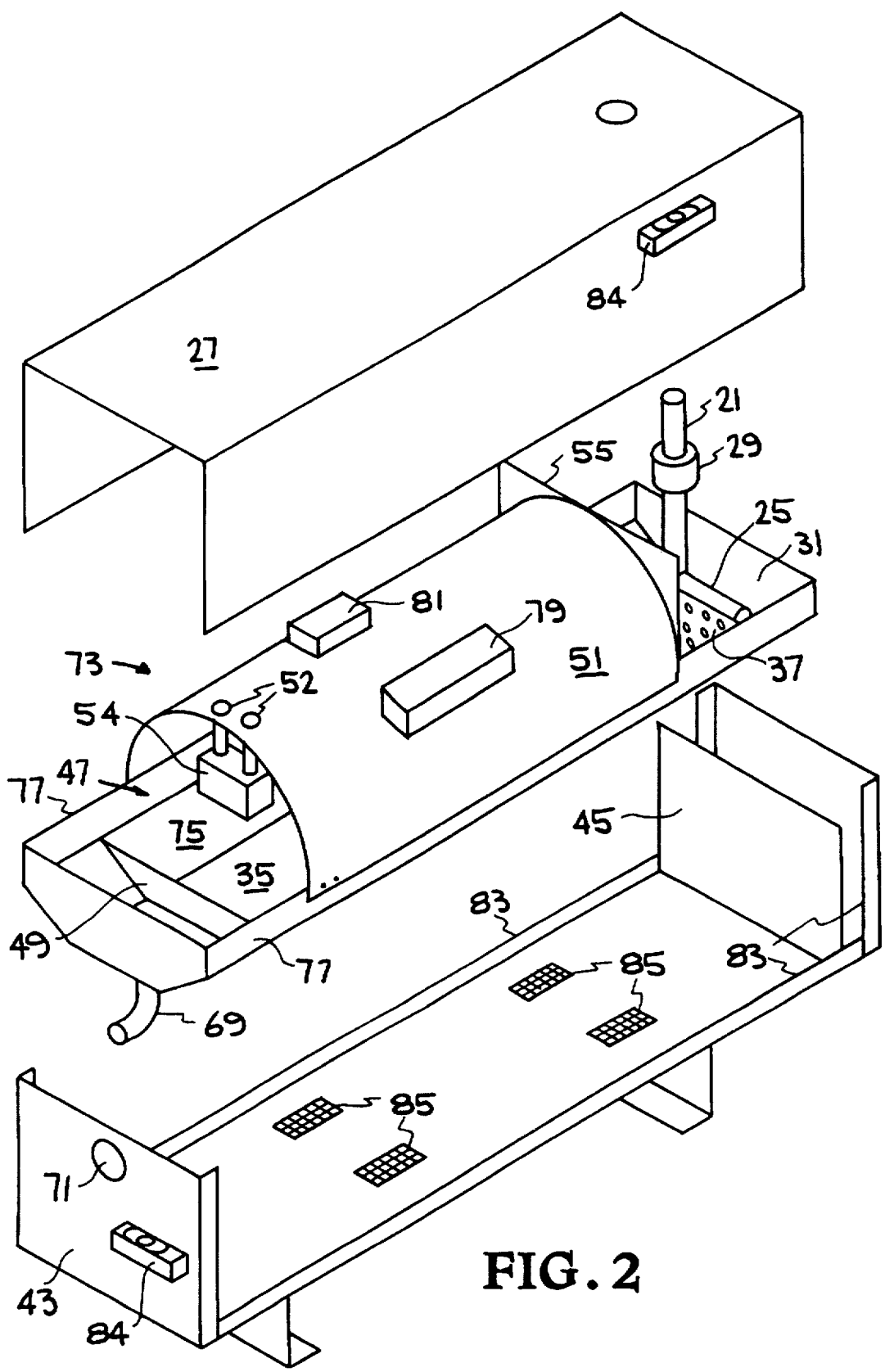
FIG. 2 is a three dimensional view of the disassembled outer casing and main tray unit.

FIG. 2 is a three dimensional view of, from top to bottom, the outer casing lid 27 (about 20×35×69 cm) with spirit level 84, main tray unit 73 (about 18×30×61 cm), and outer casing base 43 (about 18×34×66 cm). The view in FIG. 2 shows how the UV disinfector 1 is assembled and disassembled for production, cleaning and maintenance. That is, after full assembly, main tray unit 73 is set within outer casing base 43, outlet port 69 being placed through a hole in outer casing base 43, not shown in this figure. The lower surface of main tray unit 73, that is main tray floor 35, rests directly on the outer casing base 43.

In this three dimensional view, many features of the inventive UV disinfector 1 become more apparent. The main tray beveled walls 75 (about 11×61 cm) extend from the main tray floor 35 (about 10 cm×61 cm) to the main tray vertical walls 77 (about 4 cm×61 cm). The curved top reflector 51 extends and overlaps the outside surface of the main tray vertical walls 77 by 2.5 cm, where it is bolted into place, providing considerable structural stability to main tray unit 73. This configuration also allow any condensation which occurs between curved top reflector 51 and outer casing lid 27 to drain away from the treatment chamber 47, avoiding any problems with contamination, and if severe, providing an indication to the user who will observe the runoff coming from the base 43 through drain ports 85 of the extent of this problem. The drain ports 85 are typically fitted with the screen to avoid the entry of vermin, etc.

The UV lamp 53 is suspended from the curved top reflector 51 by a UV lamp support clip 56 (not seen in this figure) attached to the end reflector 55 at one end, and by the socket 54 which is attached to the curved top reflector 51 by the socket attachment bolts 52. Prior art quartz sleeve protectors for UV lamp 53 are eliminated in the present design because the UV lamp 53 is carefully suspended above the flow of the feed water 5, and also because the UV lamp 53 burns at a sufficient temperature that condensation never develops at its surface. Both the failure of moisture requirements and the heavy UV bombardment avoids the problems of biomass buildup which plagued prior art configurations.

The UV lamp 53 is powered by electrical ballast 79, this power being appropriately routed by terminal board 81. Typically, condensation develops between outer casing lid 27 and the top surface of curved top reflector 51 during the use of UV disinfector 1 due to the high humidity which naturally occurs with increased temperature in an enclosed area which contains fluids. This condensation presents a possible threat to the electrical ballast 79 and terminal board 81, as well as their connecting wires. Therefore, these electrical devices will typical have a covering of waterproof tape between them and the curved top reflector 51 to deflect dropping condensation away from them, and down the slope of curved top reflector 51 to the outer casing base 43, where the excess condensation drains from the UV disinfector 1.

The baffle wall 37 rises from the main tray floor 35 extending along the main tray beveled walls 75 upwards to the top edge of the main tray vertical walls 77. The baffle wall 37 serves to position the feed water 5 so as to provide a narrow distribution of UV dose. However, the baffle wall 37 does not limit the height of feed water 5. The height of the feed water 3 as it traverses the UV disinfector 1 is absolutely limited to the height of the main tray vertical walls 75, which are consistent throughout the flow-through processing.

The ultimate regulator of the feed water 5 level during processing in UV disinfector 1 is outlet baffle weir 49, which rises only to the juncture of the main tray beveled walls 75 and the main tray vertical walls 77. Any inappropriate height of feed water 5 which might potentially occur due to improper use or efforts to disable safety features, will be passively avoided by the overall limited height of the main tray vertical walls 77, main tray inlet wall 37, and the height of the outlet box 65. The main tray unit 73 is made about one inch smaller that the outer casing base 43 and outer casing lid 27, so there is considerable room for overflow to escape the main tray 73. The outer casing base 43 is provided with a placement lip 83 which serves to hold outer casing lid 27 in place, but provides enough clearance to allow flow of excess water out of the unit. In high humidity climates, or where consistent overflow is expected, optional drain ports 85 protected by wire screen can be provided in outer casing base 43. Spirit level 84 is positioned next to view window 71.

Figure 3:
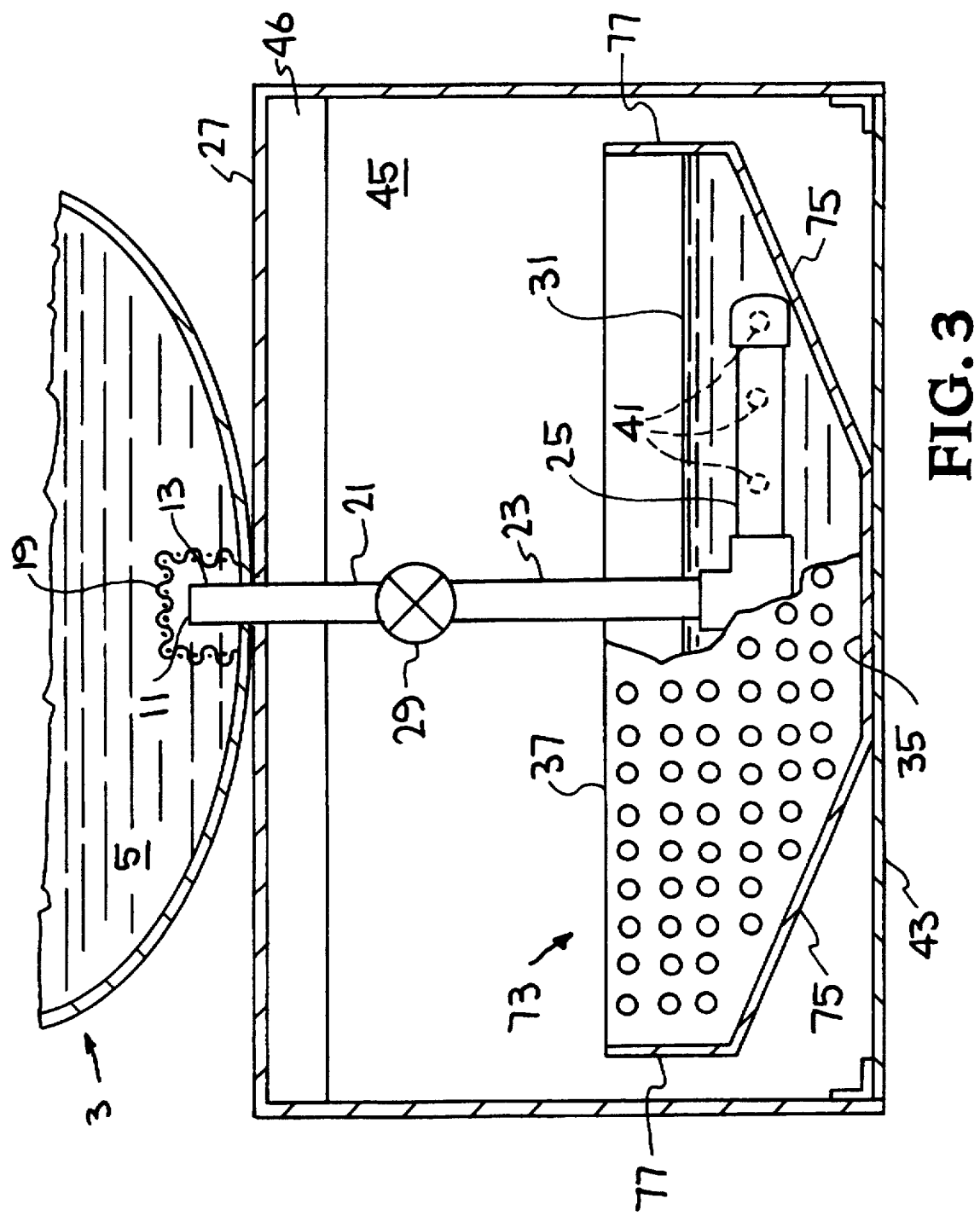
FIG. 3 is a cross sectional view of the UV disinfector at the level of the baffle wall.

FIG. 3 provides a cross sectional view of the UV disinfector 1 at the level of the baffle wall 37, showing its relation to the outer casing lid 27 and outer casing base 43. As shown, the main tray floor 35 rests directly on the outer casing base 43. The main tray beveled walls 75 then are free standing, and there is about a one inch gap between the main tray vertical walls 77 and the outer casing lid 27. The baffle wall 37 is evenly provided with baffle wall holes 64 about 0.6 cm in diameter, and spaced evenly about 2.0 cm apart. These serve to laminarize the flow of feed water 5 into treatment chamber 47 as shown in FIGS. 1 and 2.

Also in FIG. 3 is shown how the inlet manifold 21 is attached to baffle wall 37. This causes some shadowing of the laminar flow of feed water 5 directly after it traverse baffle wall 32, but not enough to compromise the laminar flow in the treatment chamber 47, as the flow is strong enough to reorient the feed water 5 in the shadowed area.

Figure 4:
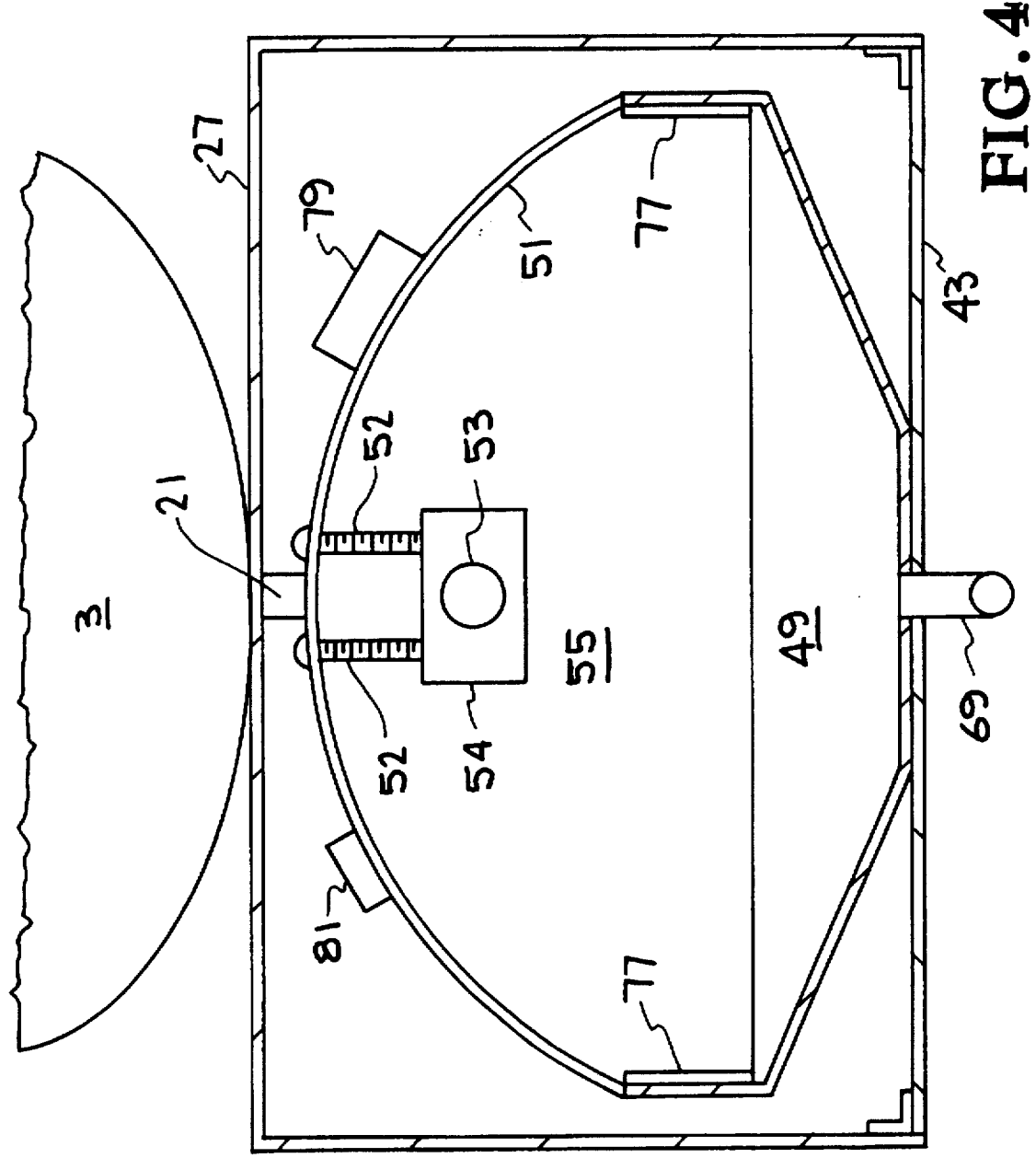
FIG. 4 is a cross sectional view of the UV disinfector at the level of the outlet baffle weir.

FIG. 4 provides a cross sectional view of the UV disinfector 1 at the level of the outlet baffle dam 49. This view makes clear that the outlet baffle dam 49 only reaches to the upper level of the main tray beveled walls 75, and ends just at the lower end of the main tray vertical walls 77.

Figure 5:
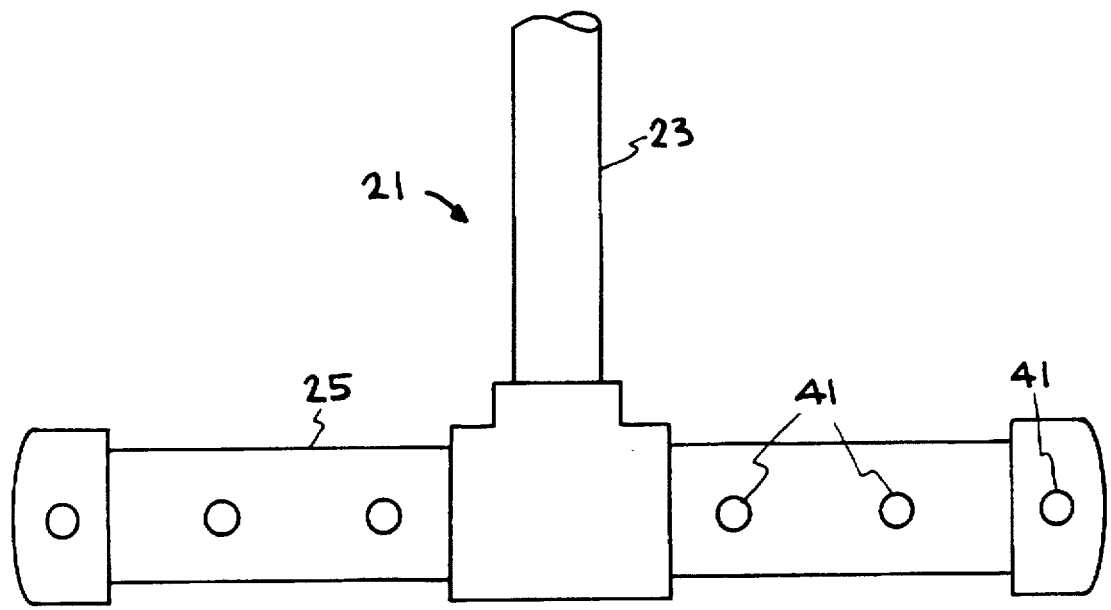
FIG. 5 is a detailed view of the inlet manifold.

FIG. 5 provides a detailed view of inlet manifold 21, including inlet feed tube 23 and inlet distribution tube 25. Distribution tube holes 41 are clearly seen in this view. Typically, they will be directing the flow of the feed water 5 towards the main tray inlet wall 33 as shown in FIG. 1.

Figure 6:
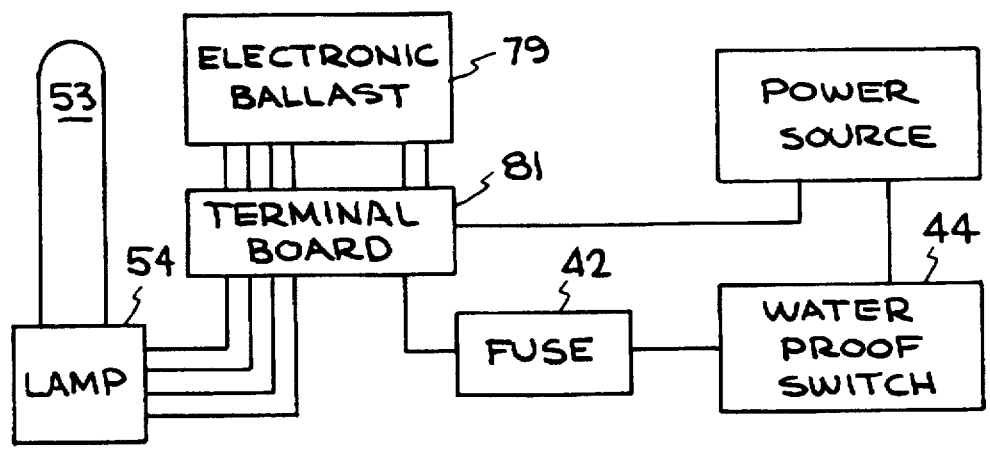
FIG. 6 is a schematic view of the electronics.

FIG. 6 provides a schematic view of terminal board 81 which regulates the flow of power to electronic ballast 79 and lamp 53 through socket 54. The fuse 42 and waterproof switch 44 are also shown in their connection to the power source.

Figure 7:
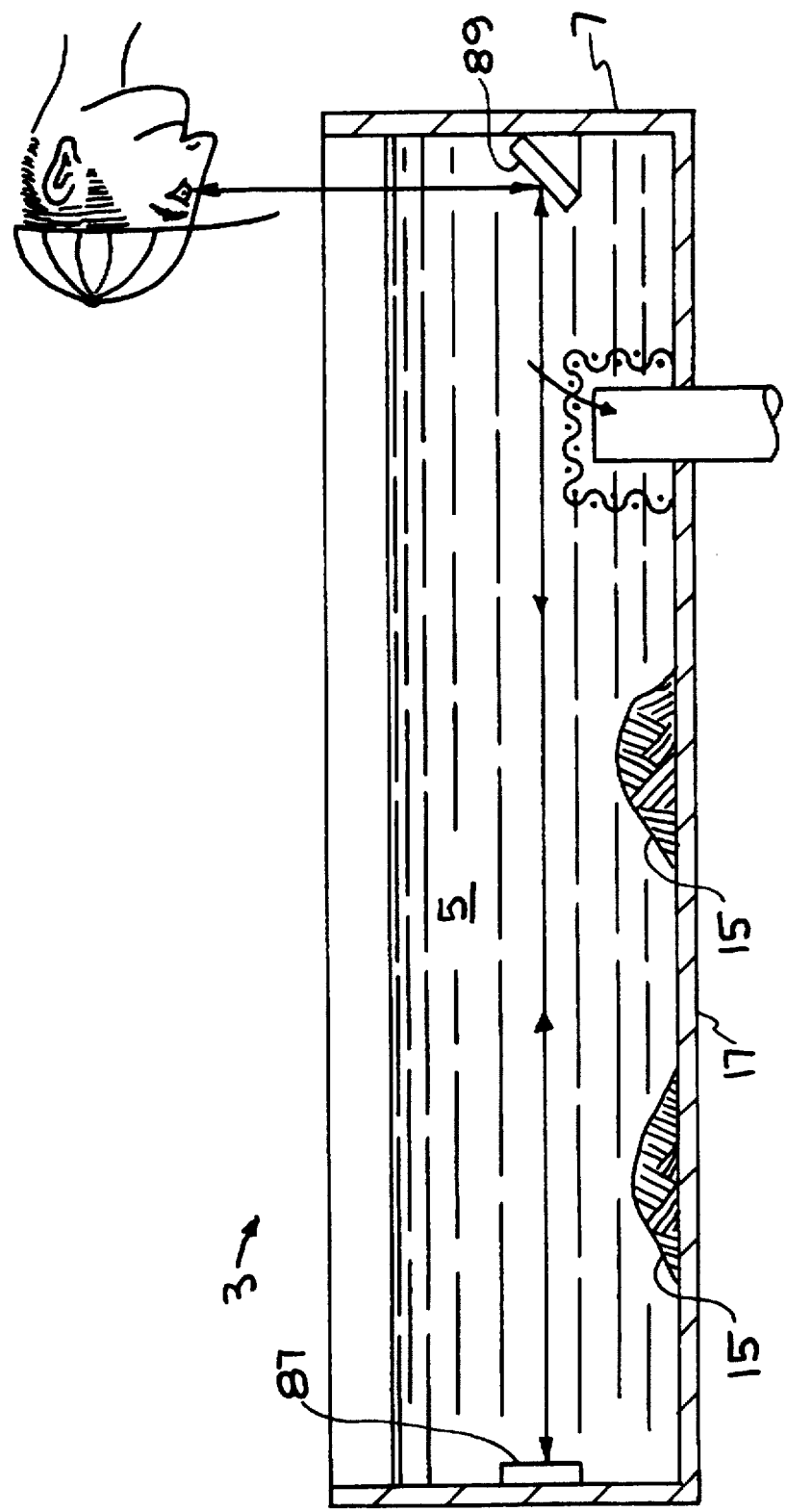
FIG. 7 is a diagram of feed water turbidity rough check.

FIG. 7 provides one approach to making a quick, rough check of the turbidity of the feed water 5 in inlet trough 3. Here, the user looks over the top of the inlet trough walls 7 to the sighting mirror 89. The sighting mirror 87 provides a view through the feed water 5 down the length of the inlet trough 3. A visual target 87 is provided on the farthest inlet trough wall 7. When the figure becomes obscure, a longer settling time is allowed, or multiple pass-through of the feed water 5 is provide to assure adequate treatment.

EXAMPLE 1

The distribution of the residence time of water in the inventive UV disinfector provides one measure of the degree to which the design is efficient. Since the water parcel with the shortest residence time must receive adequate UV exposure for disinfection, a wide distribution of residence time implies that the device is overdosing much of the water flowing through it, and potentially underdosing the parcels with shortest residence time.

A pulse of a mild acid was injected into the inlet port as the tracer, and its arrival monitored at the outlet with a pH meter. Since the pH meter provides a logarithmic repose to the tracer acid concentration, very low concentrations can also be easily detected. Based on this method, it was determined that the shortest residence time of water in one embodiment of the present invention is about 10 seconds, consistent with the design calculations.

The radiometric design of the inventive UV disinfector assumes an extinction coefficient for UV light in inlet water of 0.3 cm$^{-1}$, corresponding to the average value for water released from U.S. municipal waste water treatment plants. The dimensions of the tray and the lamp position were varied using radiometric calculations to optimize the UV exposure.

The combined germicidal performance of the inventive UV disinfector was tested by measuring its efficiency in killing marker bacteria with which the inlet water was seeded. For these tests, the inlet water was seeded with *E. coli* to obtain concentrations of 100,000 CFU (colony forming units) per 100 ml of water. For each test, the concentration of *E. coli* in the inlet water and the outlet water was measured. The inlet CFU concentration was measured with at least two different samples, and the outlet CFU concentration with at least three different samples. For these measurements, standard membrane filter tests were used, diluting the samples as needed. In these tests, a standard volume of water sample was filtered through a membrane. The membrane was then cultured with agar and incubated for 24 hours. A count of visible colonies on the membrane allowed calculation of the concentration of CFUs in the water sample.

The disinfection ability of the device is expressed with a survival ratio for *E. coli*. The survival ratio is defined as the ratio of CFU concentration in the outlet water to the CFU concentration in the inlet water. The initial measurements of the survival rate were conducted with deionized water seeded with *E. coli*. Subsequently, the tests were repeated with turbid water seeded with *E. coli*. Different degrees of turbidity (measured in Nephelometric Turbidity Units, or NTUs) were produced in the inlet water by adding measured amounts of standard kalonite clay to de-ionized water. The NTU value for the water was measured with a calibrated nephelometer from the Department of Environmental Engineering at U.C. Berkeley. The survival rate was plotted as a function of the turbidity of the inlet water, as shown in Table 1. The de-ionized water seeded with a coliform concentration of $10^5$ CFU/100 ml visually appears just a clear as ordinary tap water. Water with the $10^5$ CFU/100 ml and a turbidity of 5 NTU appears distinctly turbid when viewed in a transparent drinking cup in ordinary room light.

EXAMPLE 2

Additional inventive disinfection devices were manufactured in Bombay and their performance was tested by a commercial pathology laboratory using the World Health Organization (WHO) protocol. Distilled water spiked with *E. coli* at a concentration of 100,000 CFUs was introduced in the inlet port of the device, and the outlet water was tested for viable *E. coli* count using a cultured membrane filter. Repeated tests showed 0 or 1 CFU of *E. coli* per 100 ml of outlet water, consistent with WHO guidelines.

The water disinfection performance of another inventive device was tested at the Haffkine Institute, a national laboratory of pathology and infectious diseases in Bombay, India. In the test at the Haffkine Institute, each of the pathogenic organisms were separately suspended in 200 liters of tap water in which chlorine had been neutralized. The concentrations of the organisms were measured in the water before and after it was passed through the device. Owing to technical difficulties with water flow regulation, the tests were conducted a 22 Lpm rather than the rated 30 Lpm design flow rate. At 22 Lpm, the tests demonstrated complete elimination of the pathogens in the outlet water stream as shown in Table 2. The tests concluded that the outlet water of the device was potable from a bacteriological point of view.

Using the present inventive disinfector, UV disinfection is rapid (less than 15 seconds) and inexpensive (less than 2 ¢ per metric ton). In addition the instrumentation is easy to set up and transport. Although it does not provide residual protection, UV disinfection eliminates coliform in the outlet water (less than 1 fecal coliform per 100 milliliters) when processing inlet water with 100,000 fecal coliform per 1000 milliliters. For reference, the infectious dose Table 3 compiled by Dr. Colwell for enteric pathogens based on current data is provided (Colwell, NAS Conference, Washington, D.C., 1995). This table is given with the caveat that the infectious dose will certainly vary depending on the immunological status and general health of the exposed individual.

Given the survival ratio of $10^{-5}$ measured in the laboratory with the inventive UV disinfector, for *E. coli*, it appears likely from the data presented in Table 2 that the inventive UV disinfector would provide adequate protection from a broad range of enteric pathogens.

We claim:

1. A UV disinfector providing a narrow distribution of feed water residence time and UV dose, comprising:
   a) a gravity driven feed water delivery system,
   b) a baffle wall downstream of the feed water delivery system, the baffle wall having a plurality of spaced perforations,
   c) an air-suspended UV lamp,
   d) a treatment chamber beneath the UV lamp downstream of the baffle wall, and
   e) an outlet weir at the end of the treatment chamber, the outlet weir defining approximately equal water flow paths through the treatment chamber from each of the perforations.

2. The UV disinfector of claim 1, wherein an inlet port is provided at a specific diameter limiting inlet water flow to the correct rate.

3. The UV disinfector of claim 2, wherein the inlet port is about 1.5 cm in diameter when the inlet water flow rate is about 15 liters/minute.

4. The UV disinfector of claim 2, wherein the inlet port is about 3 cm in diameter when the inlet water flow rate is about 60 liters/minute.

5. The UV disinfector of claim 1, wherein the perforations in the baffle wall are about 10%–30% of the total area of the baffle.

6. The UV disinfector of claim 5, wherein the perforations are about 12%–20% of the total area of the baffle.

7. The UV disinfector of claim 6, wherein the perforations are about 15% of the total area of the baffle.

8. The UV disinfector of claim 1, wherein the perforations are between about 0.4 and 2.0 cm in diameter.

9. The UV disinfector of claim 8, wherein the perforations are spaced between about 0.9 and 4.2 cm apart at their centers.

10. The UV disinfector of claim 8, wherein the perforations are 0.5 and 1.0 cm in diameter.

11. The UV disinfector of claim 10, wherein the perforations are spaced between about 1.1 and 2.2 cm apart at their centers.

12. The UV disinfector of claim 10, wherein the perforations are about 0.6 cm in diameter.

13. The UV disinfector of claim 12, wherein the perforations are spaced about 1.4 cm apart at their centers.

14. The UV disinfector of claim 1, wherein the UV lamp is selected from the group consisting of a low-pressure mercury lamp, a medium-pressure mercury lamp, a high-pressure mercury lamp, and a xenon arc lamp.

15. The UV disinfector of claim 1, wherein the UV lamp is directly exposed to the treatment chamber without a protective window between the UV lamp and the treatment chamber.

16. The UV disinfector of claim 1, wherein the UV lamp is provided in multiples.

17. The UV disinfector of claim 16, wherein two UV lamps are provided and the flow rate is adjusted to 8 gallons of feed water per minute.

18. The UV disinfector of claim 1, wherein the off/on status of the UV lamp can be directly observed during processing.

19. The UV disinfector of claim 1, wherein the treatment chamber is provided with walls angled so as to provide a narrow residence time and narrow UV exposure distribution to the feed water.

20. The UV disinfector of claim 19, wherein the treatment chamber is provided with straight-edged beveling.

21. The UV disinfector of claim 19, wherein the treatment chamber is provided with a semi-circular beveling.

22. The UV disinfector of claim 19, wherein the treatment chamber is provided with about an inverted Gaussian shape.

23. The UV disinfector of claim 19, wherein parallel channels with beveling are provided, each with its own UV lamp.

24. The UV disinfector of claim 19, wherein the walls of the treatment chamber are limited in height, so that excessive feed water levels will fall free of the UV disinfector.

25. The UV disinfector of claim 1, wherein the outlet weir is about half the height of the baffle wall.

26. The UV disinfector of claim 1, wherein the UV disinfector has dimensions of within about 5 m×2 m×2 m.

27. The UV disinfector of claim 26, wherein the UV disinfector has dimensions of within about 120 m×25 cm×25 cm.

28. The UV disinfector of claim 27, wherein the UV disinfector has dimensions of within about 30 cm×15 cm×15 cm.

29. The UV disinfector of claim 1, wherein the feed water is treated at a rate of about 4 gallons per minute, there is about a 2–5 second wide distribution of residence time of 99% of a detection aliquot.

30. The UV disinfector of claim 29, wherein there is about a 3–4.5 second wide distribution of residence time.

31. The UV disinfector of claim 30, wherein there is a about a 4 second wide distribution of residence time.

32. The UV water disinfector of claim 1, wherein the water supplied at atmospheric pressure is disinfected at a rate of between about 2 to 6 gallons per minute.

33. The disinfector of claim 32, wherein the rate is from between about 3 to 5 gallons per minute.

34. The disinfector of claim 33, wherein the rate is about 4 gallons per minute.

35. The use of the UV water disinfector of claim 1 when used for serum disinfection, wherein the exit water receives a UV energy dose of about 110–150 Milliwatt-sec/cm$^2$.

36. The use of the UV water disinfector of claim 1, when used to produce potable water, wherein the exit water receives a UV energy dose of at least about 40 Milliwatt-sec/cm$^2$.

37. The UV water disinfector of claim 1, when used for effluent treatment or fish culture purposes, wherein the exit water receives a UV energy dose of at least about 20 Milliwatt-sec/cm$^2$.

38. The UV disinfector of claim 1, which reduces viable pathogene levels in feed water containing E. Coli at 1.2×10$^5$/100 ml, Salmonella Typhi at 1.3×10$^4$/100 ml, Vibreo Cholerae at 1.7×10$^4$/100 ml, Str. faecalis at 1.8×10$^3$/100 ml, Cl. Welchii at 5.6×10$^4$/100 ml, Shigella Dysenteriae at 1.7×10$^4$/100 ml, Proteus Vulgaris at 1.4×10$^4$/100 ml, Klebsiella Aerogens at 2.1×10$^4$/100 ml, Ent. Eloaceae at 1.9×10$^4$/100 ml, or Pseudomonas aeruginosa at 2.5×10$^4$/100 ml to less than one viable pathogen per 100 ml of feed water.

39. A UV fluid disinfector, comprising:

a gravity driven feed fluid delivery system;

a generally vertical baffle wall downstream of the feed fluid delivery system, the baffle wall having a plurality of spaced perforations oriented for horizontal fluid flow therethrough;

a treatment chamber immediately downstream of the baffle wall such that the baffle wall defines a first end of the treatment chamber, the chamber including a generally horizontal fluid tray;

a UV lamp positioned to irradiate fluid in the fluid tray; and an outlet positioned at a second, opposite end of the treatment chamber.

40. The UV fluid disinfector of claim 39, further comprising a generally vertical elevated wall downstream of the baffle wall and upstream of the outlet, the elevated wall extending below the surface of fluid in the fluid tray while allowing fluid flow thereunder.

41. A UV water disinfector, comprising:

a feed water delivery system communicating with an inlet chamber;

a treatment chamber downstream of the inlet chamber, the treatment chamber including a water tray; and a UV lamp positioned above the water tray to irradiate water in the water tray; and a baffle wall separating the the inlet chamber from the treatment chamber, the baffle wall including a plurality of spaced perforations configured to suppress introduction of turbulence from the inlet chamber to water flow within the water tray.

* * * * *

EX PARTE REEXAMINATION CERTIFICATE (5753rd)

United States Patent
Gadgil et al.

(10) Number: US 5,780,860 C1
(45) Certificate Issued: May 1, 2007

(54) UV WATER DISINFECTOR

(75) Inventors: Ashok Gadgil, El Cerrito, CA (US); Vikas Garud, Bombay (IN)

(73) Assignee: The Regents of the University of California, Oakland, CA (US)

Reexamination Request:
No. 90/005,657, Mar. 2, 2000

Reexamination Certificate for:
Patent No.: 5,780,860
Issued: Jul. 14, 1998
Appl. No.: 08/692,558
Filed: Aug. 6, 1996

Related U.S. Application Data

(60) Provisional application No. 60/003,485, filed on Sep. 8, 1995.

(51) Int. Cl.
*A61L 2/10* (2006.01)

(52) U.S. Cl. .................. 250/432 R; 250/434; 250/435; 422/24

(58) Field of Classification Search ............. 250/432 R, 250/434, 435; 422/24
See application file for complete search history.

(56) References Cited

U.S. PATENT DOCUMENTS

| | | |
|---|---|---|
| 2,504,349 A | 4/1950 | Pietro |
| 3,491,234 A | 1/1970 | Wiltrout |
| 3,562,520 A | 2/1971 | Hippen |
| 3,710,111 A | 1/1973 | Collura |
| 3,858,048 A | 12/1974 | Shand et al. |
| 4,201,916 A | 5/1980 | Ellner |
| 4,304,996 A | 12/1981 | Blades |
| 4,622,465 A | 11/1986 | Harig et al. |
| 4,629,896 A | 12/1986 | Bridgen |
| 4,661,264 A | 4/1987 | Goudy, Jr. |
| 4,742,231 A | 5/1988 | Bridgen |
| 5,230,792 A | 7/1993 | Sauska et al. |
| RE34,513 E | 1/1994 | Ellner |
| 5,420,432 A | 5/1995 | Manook et al. |
| 5,441,179 A | 8/1995 | Marsh |
| 5,597,487 A | 1/1997 | Vogel et al. |
| 5,660,719 A | 8/1997 | Kurtz et al. |
| 5,900,212 A | 5/1999 | Maiden et al. |

OTHER PUBLICATIONS

Applications of Germicidal, Erythemal and Infrared Energy, Matthew Luckiesh, D Sc , D E , D Van Nostrand Co , Inc New York, NY, 1946, pp. foreward, 231–269, 441–451.

*Primary Examiner*—Kiet T. Nguyen

(57) ABSTRACT

A UV disinfector with a gravity driven feed water delivery system, and an air-suspended bare UV lamp. The disinfector is hydrodynamically optimized with a laminerizing, perforated baffle wall, beveled treatment chamber, and outlet weir.

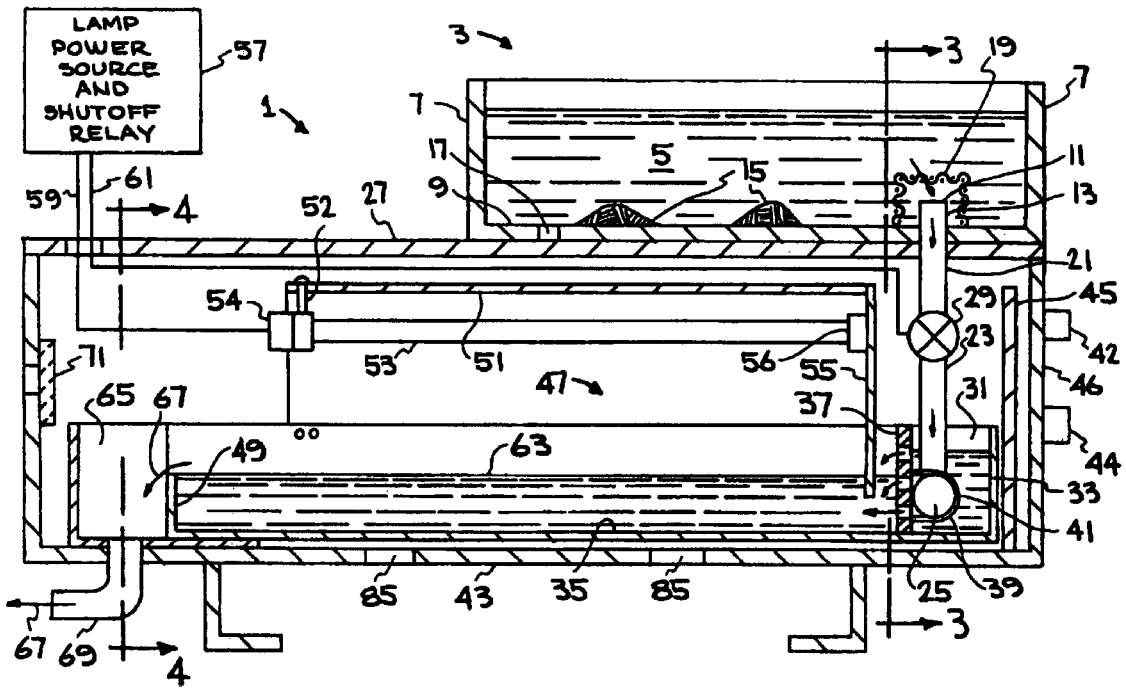

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 17, 18, 20–24, 27, 29, 32 and 35–41 are determined to be patentable as amended.

Claims 3–16, 19, 25–26, 28, 30–31 and 33–34, dependent on an amended claim, are determined to be patentable.

1. A UV disinfector providing a [narrow distribution of feed water residence time and UV dose] *normalized or uniform dose of UV light*, comprising:
   a) a gravity driven feed water delivery system,
   b) a baffle wall downstream of the feed water delivery system, the baffle wall having a plurality of spaced perforations *distributed between a top of the baffle wall to a bottom of the baffle wall*,
   c) an air-suspended UV lamp,
   d) a treatment chamber beneath the UV lamp downstream of the baffle wall, and
   e) an outlet weir at the end of the treatment chamber, [the outlet weir defining approximately equal water flow paths through the treatment chamber from each of the perforations]
   *wherein the perforations and the treatment chamber are configured to produce a substantially non-recirculating flow of water in the treatment chamber, such that the water moving from the baffle wall to the outlet weir is continuously replaced by water flowing through the perforations; and,*
   *whereby the treatment chamber is shaped and combined with the UV lamp such that all water inside the treatment chamber has received the normalized or uniform dose of UV light from the UV lamp.*

2. The UV disinfector of claim 1, wherein *the gravity driven feed water delivery system comprises* an inlet port [is provided at] *comprising* a specific diameter limiting inlet water flow to [the correct] *a* rate.

17. The UV disinfector of claim [16] *1*, wherein two UV lamps are provided and the flow rate is adjusted to 8 gallons of feed water per minute.

18. The UV disinfector of claim 1[, wherein the] *configured such that* off/on status of the UV lamp can be directly observed during processing.

20. The UV disinfector of claim [19] *1*, wherein the treatment chamber is provided with straight-edged beveling.

21. The UV disinfector of claim [19] *1*, wherein the treatment chamber is provided with a semi-circular beveling.

22. The UV disinfector of claim [19] *1*, wherein the treatment chamber is provided with about an inverted Gaussian shape.

23. The UV disinfector of claim [19] *1*, wherein parallel channels with beveling are provided, each with its own UV lamp.

24. The UV disinfector of claim 19, [wherein the] *comprising vertical* walls of the treatment chamber [are] limited in height, so that excessive feed water levels will fall free of the UV disinfector.

27. The UV disinfector of claim 26, wherein the UV disinfector has dimensions of within about 120 [m] *cm*×25 cm×25 cm.

29. The UV disinfector of claim [1] *2*, wherein [the] feed water is treated at a rate of about 4 gallons per minute, *and* there is about a 2–5 second wide distribution of residence time of 99% of a detection aliquot.

32. The UV water disinfector of claim 1, [wherein the] *configured such that* water supplied at atmospheric pressure is disinfected at a rate of between about 2 to 6 gallons per minute.

35. [The use] *Use* of [the] *a* UV water disinfector [of claim 1 when used] for serum disinfection, *comprising:*
   *providing a UV disinfector that provides normalized or uniform dose of UV light, the disinfector comprising*
      *a) a gravity driven feed water delivery system,*
      *b) a baffle wall downstream of the feed water delivery system, the baffle wall having a plurality of spaced perforations distributed between a top of the baffle wall to a bottom of the baffle wall,*
      *c) an air-suspended UV lamp,*
      *d) a treatment chamber beneath the UV lamp downstream of the baffle wall, and*
      *e) an outlet weir at the end of the treatment chamber, wherein the perforations and the treatment chamber are configured to produce a substantially non-recirculating flow of water in the treatment chamber, such that the water moving from the baffle wall to the outlet weir is continuously replaced by water flowing through the perforations; and,*
      *whereby the treatment chamber is shaped and combined with the UV lamp such that all water inside the treatment chamber has received the normalized or uniform dose of UV light from the UV lamp;*
   *delivering serum to the UV disinfector, and*
   wherein [the] *an* exit [water] *serum* receives a UV energy dose of about 110–150 Milliwatt-sec/cm$^2$.

36. [The use] *Use* of [the] *a* UV water disinfector [of claim 1, when used] to produce potable water, *comprising:*
   *providing a UV disinfector that provides normalized or uniform dose of UV light, the disinfector comprising*
      *a) a gravity driven feed water delivery system,*
      *b) a baffle wall downstream of the feed water delivery system, the baffle wall having a plurality of spaced perforations distributed between a top of the baffle wall to a bottom of the baffle wall,*
      *c) an air-suspended UV lamp,*
      *d) a treatment chamber beneath the UV lamp downstream of the baffle wall, and*
      *e) an outlet weir at the end of the treatment chamber, wherein the perforations and the treatment chamber are configured to produce a substantially non-recirculating flow of water in the treatment chamber, such that the water moving from the baffle wall to the outlet weir is continuously replaced by water flowing through the perforations; and,*
      *whereby the treatment chamber is shaped and combined with the UV lamp such that all water inside the treatment chamber has received the normalized or uniform dose of UV light from the UV lamp;*
   wherein [the] *an* exit water receives a UV energy dose of at least about 40 Milliwatt-sec/cm$^2$.

37. [The] *Use of a* UV water disinfector [of claim 1, when used], for effluent treatment or fish culture purposes, *comprising:*

*providing a UV disinfector that provides normalized or uniform dose of UV light, the disinfector comprising*
a) *a gravity driven feed water delivery system,*
b) *a baffle wall downstream of the feed water delivery system, the baffle wall having a plurality of spaced perforations distributed between a top of the baffle wall to a bottom of the baffle wall,*
c) *an air-suspended UV lamp,*
d) *a treatment chamber beneath the UV lamp downstream of the baffle wall, and*
e) *an outlet weir at the end of the treatment chamber, wherein the perforations and the treatment chamber are configured to produce a substantially non-recirculating flow of water in the treatment chamber, such that the water moving from the baffle wall to the outlet weir is continuously replaced by water flowing through the perforations; and,*
*whereby the treatment chamber is shaped and combined with the UV lamp such that all water inside the treatment chamber has received the normalized or uniform dose of UV light from the UV lamp;*
*delivering water to the UV disinfector that comprises sanitary device treatment effluent or comprises fish culture water, and*
wherein [the] *an* exit water receives a UV energy dose of at least about 20 Milliwatt-sec/cm$^2$.

38. The UV disinfector of claim 1, which reduces viable [pathogene] *pathogen* levels in feed water containing E. [Coli] *coli* at 1.2×10$^5$/100 ml, Salmonella [Typhi] *typhi* at 1.3×10$^4$/100 ml, Vibreo [Cholerae] *cholerae* at 1.7×10$^4$/100 ml, Str. faecalis at 1.8×10$^3$/100 ml, Cl. [Welchii] *welchii* at 5.6×10$^4$/100 ml, Shigella [Dysenteriae] *dysenteriae* at 1.7×10$^4$/100 ml, Proteus [Vulgaris] *vulgaris* at 1.4×10$^4$/100 ml, Klebsiella [Aerogens] *aerogens* at 2.1×10$^4$/100 ml, Ent. [Eloaceae] *eloaceae* at 1.9×10$^4$/100 ml, or Pseudomonas aeruginosa at 2.5×10$^4$/100 ml to less than one viable pathogen per 100 ml of feed water.

39. A UV fluid disinfector, comprising:
a gravity driven feed fluid delivery system;
a generally vertical baffle wall downstream of the feed fluid delivery system, the baffle wall having a plurality of spaced perforations oriented for horizontal fluid flow therethrough;
a treatment chamber immediately downstream of the baffle wall such that the baffle wall defines a first end of the treatment chamber, the chamber including a generally horizontal fluid tray *comprising beveled or sloped walls*;
a UV lamp positioned to irradiate *and provide a uniform light dose to* fluid in the fluid tray; and
an outlet *weir* positioned at a second, opposite end of the treatment chamber;
*wherein the fluid tray, outlet weir, and perforations define a fluid depth and flow rate of fluid within the fluid tray from the baffle wall to the outlet weir, the fluid depth and flow rate ensuring that all the fluid that flows over the outlet weir has received a normalized or uniform dose of UV light from the UV lamp.*

40. The UV fluid disinfector of claim 39, further comprising a generally vertical elevated wall downstream of the baffle wall and upstream of the outlet *weir*, the elevated wall extending below the surface of fluid in the fluid tray while allowing fluid flow thereunder.

41. A UV water disinfector, comprising:
a feed water delivery system communicating with an inlet chamber;
a treatment chamber downstream of the inlet chamber, the treatment chamber including a water tray, *two sides of a bottom surface of the water tray being beveled or sloped;*
*the water tray comprising a fluid exit;* [and]
a UV lamp positioned above the water tray to irradiate water in the water tray; and
a baffle wall separating the inlet chamber from the treatment chamber, the baffle wall including a plurality of spaced perforations configured to suppress introduction of turbulence from the inlet chamber to water [flow] within the water tray;
*wherein the plurality of spaced perforations and the water tray are shaped such that water inside the water tray receives a uniform light dose from the UV lamp when water exits the water tray, the perforations and the water tray combining to produce a substantially non-recirculating flow of water in the water tray, such that the water moving through the water tray is continuously replaced by water flowing through the plurality of spaced perforations.*

\* \* \* \* \*